(12) United States Patent
Stránská et al.

(10) Patent No.: US 12,194,158 B2
(45) Date of Patent: Jan. 14, 2025

(54) OROMUCOSAL NANOFIBER CARRIERS FOR THERAPEUTIC TREATMENT

(71) Applicant: Instar Technologies A.S., Liberec (CZ)

(72) Inventors: Denisa Stránská, Liberec (CZ); Jana Svobodova, Liberec (CZ); Pavel Berka, Prague (CZ); Pavel Doležal, Hradec Králové (CZ)

(73) Assignee: INSTAR TECHNOLOGIES A.S., Liberec (CZ)

( * ) Notice: Subject to any disclaimer, the term of this patent is extended or adjusted under 35 U.S.C. 154(b) by 887 days.

(21) Appl. No.: 16/071,710

(22) PCT Filed: Jan. 27, 2017

(86) PCT No.: PCT/IB2017/050428
§ 371 (c)(1),
(2) Date: Jul. 20, 2018

(87) PCT Pub. No.: WO2017/130141
PCT Pub. Date: Aug. 3, 2017

(65) Prior Publication Data
US 2021/0069122 A1    Mar. 11, 2021

Related U.S. Application Data

(60) Provisional application No. 62/439,324, filed on Dec. 27, 2016, provisional application No. 62/287,863, filed on Jan. 27, 2016.

(51) Int. Cl.
| A61K 9/70 | (2006.01) |
| A61K 31/4196 | (2006.01) |
| A61K 31/4439 | (2006.01) |
| A61K 45/06 | (2006.01) |

(52) U.S. Cl.
CPC ............ *A61K 9/70* (2013.01); *A61K 31/4196* (2013.01); *A61K 31/4439* (2013.01); *A61K 45/06* (2013.01)

(58) Field of Classification Search
None
See application file for complete search history.

(56) References Cited

U.S. PATENT DOCUMENTS

| 9,789,060 | B2 * | 10/2017 | Stranska ............... A61K 9/006 |
| 2005/0226925 | A1 | 10/2005 | Singh | |
| 2010/0291160 | A1 * | 11/2010 | Carver .................. A61K 45/06 514/56 |
| 2013/0323296 | A1 | 5/2013 | Stranska et al. | |
| 2014/0242145 | A1 | 8/2014 | Yoo et al. | |

FOREIGN PATENT DOCUMENTS

| CN | 103338756 | | 10/2013 | |
| CN | 103338756 A | | 10/2013 | |
| EP | 2589692 A1 | | 5/2013 | |
| JP | 2003521493 A | | 7/2003 | |
| JP | 2010529025 A | | 8/2010 | |
| JP | 2012030581 A | | 2/2012 | |
| JP | 2013544259 A | | 12/2013 | |
| JP | 2014055119 A | | 3/2014 | |
| JP | 2015500823 A | | 1/2015 | |
| JP | 2015533171 A | | 11/2015 | |
| KR | 100806412 B1 | | 2/2008 | |
| KR | 101386096 | | 4/2014 | |
| KR | 101386096 B1 | | 4/2014 | |
| KR | 1020150051826 A | | 10/2016 | |
| RU | 2343903 C2 | | 1/2009 | |
| WO | WO-0154667 A1 * | | 8/2001 | ............ A61K 47/50 |
| WO | 03059390 A1 | | 7/2003 | |
| WO | WO-2012097763 A2 * | | 7/2012 | ............ A61K 9/006 |
| WO | 2014131376 A1 | | 9/2014 | |
| WO | 2014190038 A2 | | 11/2014 | |

OTHER PUBLICATIONS

Petr Vrbtata, Electrospun drug loaded membranes for sublingual administration of sumatriptan and naproxen, 2013, International Journal of Pharmaceutics, 457 (2013) pp. 168-176 (Year: 2013).*
American Senior Communities, Is Diabetes Preventable?, Feb. 16, 2015, American Senior Communities (Year: 2015).*
Xue Li, Synergetic taste masking of lipid coating and beta-cyclodextrin inclusion, Mar. 2014, 49(3):392-8 (Year: 2014).*
Lan He, Anti-inflammatory effects of exedin-4, a glucagon-like peptide-1 analog, on human peripheral lymphocytes in patients with type 2 diabetes, Jul. 2013, Journal of Diabetes Investigation, vol. 4, issue 4. (Year: 2013).*
Nadia M. Krasner, Glucagon-Like Peptide-1 (GLP-1) Analog Liraglutide Inhibits Endothelial Cell Inflammation through a Calcium and AMPK Dependent Mechanism, May 2014, PLOS One, vol. 9, isse 5 (Year: 2014).*
Mark K. Gutniak, Potential Therapeutic Levels of Glucagon-like Peptide I Achieved in Humans by a Buccal Tablet, Aug. 1996, Diabetes Care, vol. 19, No. 8. (Year: 1996).*
Christina Tang, Effect of pH on Protein Distribution in Electrospun PVA/BSA Composite Nanofibers, 2012, Biomacromolecules, 13, 1269-1278 (Year: 2012).*
Vrbata, Petr et al.: "Electrospun drug loaded membranes for sublingual administration of sumatriptan and naproxen", International Journal of Pharmaceutics, vol. 457, No. 1, 2013, pp. 168-176, XP028768800, ISSN: 0378-5173.
D Karthikeyan et al.: "Development of Fast Dissolving Oral Film Containing of Rizatriptan Benzoate as an Antimigraine Medication", Indo American Journal of Pharmaceutical Research, Jan. 1, 2013, XP055351933.

(Continued)

*Primary Examiner* — Abigail Vanhorn
*Assistant Examiner* — Ali S Saeed
(74) *Attorney, Agent, or Firm* — Rimon PC

(57) ABSTRACT

The present disclosure relates to oromucosal nanofiber carriers that are mucoadhesive or comprise a mucoadhesive agent for administration of active agents, including substances for their preparation, methods of preparation, and methods of use.

6 Claims, 6 Drawing Sheets

(56) References Cited

OTHER PUBLICATIONS

Zhang et al: "Coaxial Electrospinning of (Fluorescein Isothiocyanate-Conjugated Bovine Serum Albumin)-Encapsulated Poly(ε-caprolactone) Nanofibers for Sustained Release", American Chemical Society, Mar. 9, 2006, pp. 1049-1057, vol. 7 (4), Singapore.

Liao et al: "Aligned core-shell nanofibers delivering bioactive proteins", Nanomedicine, Dec. 8, 2006, pp. 465-471, vol. 1 (4).

Tsuchiya et al: Development of Mucoadhesive Film Containing Lorazepam II—Preparation and Characterization of Bilayered Sublingual Film to Avoid the Loss of Drug due to Salivary Flow in Oral Cavity, Journal of Pharmaceutical Science and Technology, Japan, 2010, pp. 133-140, vol. 70, No. 2, Japan.

Ju Son et al: "Therapeutic applications of electrospun nanofibers for drug delivery systems", Pharmacal Research, 2014, pp. 69-78, vol. 34, Korea.

Gutniak, M. et al. "Potential Therapeutic Levels of Glucagon-like Peptide I Achieved in Humans by a Buccal Tablet" Diabetes Care, American Diabetes Ass., vol. 19. No. 8 (1996), pp. 843-848.

Michael J. et al., "Oral Mucosal Drug Delivery and Therapy" Advances in Delivery Science and Technology, (2015): pp. 13-14.

\* cited by examiner

OROMUCOSAL NANOFIBER CARRIERS FOR THERAPEUTIC TREATMENT

CROSS-REFERENCE TO RELATED APPLICATIONS

This application is a United States national stage entry of International Application serial no. PCT/IB2017/050428 filed Jan. 27, 2017 which claims priority to U.S. Provisional Application No. 62/439,324, filed Dec. 27, 2016, and U.S. Provisional Application No. 62/287,863 filed Jan. 27, 2016. Each of these applications is incorporated herein by reference in its entirety.

TECHNICAL FIELD

The present disclosure relates to the preparation and administration of active agents using oromucosal nanofiber carriers that are mucoadhesive or comprise a mucoadhesive agent.

BACKGROUND OF THE INVENTION

Migraine is a chronic and episodic headache syndrome, often associated with nausea and vomiting, that affects approximately about 15 to 20% of the population of developed countries. There are two main types of migraine, with and without aura, affecting about 15% and 8% of this population, respectively. In the non-aura type, the headache is unilateral, pulsating, and moderate to severe in intensity and often including nausea and other symptoms, lasting a few hours to a few days. In the aura variety, an aura (e.g., including visual, somatosensory, and motor symptoms), develop prior to the development of a migraine attack.

Migraine pharmacological treatment regimens include the use of both over the counter (OTC) analgesics or prescriptions only medicine analgesics and several drugs belonging to the group of ergotamine and its derivatives, nonsteroidal anti-inflammatory drugs (NSAIDs) and mainly triptans, alone or in combinations. These active agents (drugs) are administered mainly by oral, rectal, parenteral (intravenous, subcutaneous), inhalation, intranasal, transdermal (including iontophoretic preparations), and oromucosal (buccal and sublingual) routes. Overall, there is still a therapeutic need of non-invasive medicated preparations possessing faster onset of the anti-migraine effect, possessing higher and safer efficacy of anti-migraine drugs.

Also, there is a need in the art for increasing bioavailability of administered drugs, including high molecular weight moieties including large and small molecule active agents, for increased efficacy and a decrease of detrimental side effects. That preparation could offer administration of active agents without a danger of lack of therapeutic effect due to vomiting frequently linked to oral administration and/or low efficacy connected with nasal or pulmonary absorption, with short lasting lag-time and without personal discomfort connected with rectal administration of suppositories and all complications connected with invasive parenteral administration, including not only pain but also generally hard sterility requirements, and also final price of medicated products. The present disclosure addresses this and other related needs in the art.

SUMMARY

In one embodiment, a polymer solution is provided for preparing an electrospun active layer of an oromucosal carrier, comprising: a migraine medication active agent comprising between about 3% to 5%, or between about 1% to 10%, of the polymer solution; a water soluble and/or biodegradable polymer comprising between about 9% to 11%, or between about 5% to 15%, of the polymer solution; a taste masking agent, pH adjusting agent, and/or a surfactant; and water comprising between about 80% to 85%, or between about 70% to 90%, of the polymer solution. Often, the polymer comprises a mixture of two or more, three or more, or four or more, different polymers. Often, when included, the taste masking agent comprises about or less than 1%, or less than about 0.5%, of the polymer solution. Also often, when included, the pH adjusting agent comprises about or less than 2% of the polymer solution. In frequent embodiments, the taste masking agent and/or the pH adjusting agent each individually comprise a combination of two or more different agents. Percentages are by weight.

A carrier for administering an oromucosal dose of a migraine treatment may also be provided, comprising a protective layer, an active layer, and a mucoadhesive layer, wherein the protective layer, the active layer, and the mucoadhesive layers are situated adjacent and coextensive with each other, and wherein the protective layer and the active layer are comprised of nanofibers, and the migraine medication is present in the active layer. Often, the migraine medication comprises a triptan. Also often, the migraine medication comprises a rizatriptan. In frequent embodiments, the migraine medication comprises rizatriptan, naratriptan, zolmitriptan, eletriptan, almotriptan, frovatriptan, avitriptan, and donitriptan.

A carrier is often provided for oromucosal delivery of a migraine medication, comprising a nanofiber active layer containing a migraine medication active agent comprising between about 23% to 32%, or between about 10% to 45%, of the nanofiber active layer; a water soluble and/or biodegradable polymer comprising between about 62% to 73%, or between about 50% to 80%, of the nanofiber active layer; a taste masking agent; and a mucoadhesive layer. Often, the nanofiber active layer is produced by needle-free electrospinning. Often, the water soluble and/or biodegradable polymer comprises a mixture of two or more, three or more, or four or more, different polymers.

In certain embodiments, a method of producing an active layer of an oromucosal carrier is provided comprising using the polymer solutions described herein in an electrospinning process. Most frequently, the active layer is deposited on an electrospun nanofiber protective layer.

Methods of treating a subject afflicted with a migraine are also provided, comprising administering the carrier to the mouth of the subject. The administering often comprises applying the mucoadhesive layer of the carrier to an oromucosal surface of the subject.

Often, the taste masking agent is selected from the groups consisting of sucralose, erythritol, isomaltitol, D-maltitol, mactitol, D-mannitol, neotame, saccharin, dextrose, sorbitol, xylitol, rebaudioside A, thaumatin, D-limonene, citral, citronellyl formate, methyl ionone, menthol, thymol, and eugenol.

Also often, the pH adjusting agent is selected from the groups consisting of sodium hydroxide (NaOH), kalium hydroxide (KOH), a sodium (bi)carbonate, a mono- or disodium phosphate, triethanolamine, citric acid, lactic acid, acetic acid, ascorbic acid, malic acid, gluconic acid, glutamic acid, hydrochloric acid, sulfuric acid, phosphoric acid, succinic acid, tartaric acid, butyric acid, arginine hydrochloride, and creatinine.

In frequent embodiments, the surfactant is selected from the groups consisting of an anionic surfactant, a non-ionic surfactant, a cationic surfactant, a fatty acid or derivative thereof, and a bile salt.

Often, the taste masking agent, pH adjusting agent, and/or surfactant comprise between about 1% to 5%, or between about 1% to 8%, of the polymer solution.

In frequent embodiments, the migraine medication comprises a triptan. Often, the migraine medication comprises a rizatriptan. Also often, the migraine medication comprises rizatriptan, naratriptan, zolmitriptan, eletriptan, almotriptan, frovatriptan, avitriptan, and donitriptan.

Active agents in addition to or alternative to migraine medications are contemplated herein. The present methods and devices provide for the incorporation of an active agent having a variety of molecular weights incorporated in the nanofibers and carriers described herein. Active agents may comprise small or large molecule moieties. For example, in certain embodiments the active agent comprises a biopolymer such as a polypeptide, a protein, a nucleic acid, a polysaccharide, a peptide, a carbohydrate, DNA, RNA, or a lipid. In certain embodiments, active agent polymers of up to about 67 kDa or 70 kDa are provided together with water soluble and/or biodegradable polymers in the present nanofibers and carriers. In certain embodiments, active agent polymers of from about 269 Daltons up to about 67 kDa are provided together with water soluble and/or biodegradable polymers in the present nanofibers and carriers. In certain embodiments, active agent polymers of from about 269 Daltons up to about 627 Daltons are provided together with water soluble and/or biodegradable polymers in the present nanofibers and carriers. In certain embodiments, active agent polymers of from about 627 Daltons up to about 4 kDa are provided together with water soluble and/or biodegradable polymers in the present nanofibers and carriers. In certain embodiments, active agent polymers of from about 3.7 kDa up to about 67 kDa are provided together with water soluble and/or biodegradable polymers in the present nanofibers and carriers.

In certain embodiments, a nanofiber and/or carrier is provided comprising a water soluble and/or biodegradable polymer and bovine serum albumin (BSA) or human serum albumin, or fragment, analog, or peptide thereof. The nanofiber, in certain embodiments, nanofiber comprises between about 5% to 20% of the bovine serum albumin and between about 80% to 95% of the water soluble and/or biodegradable polymer comprising. Often, the BSA, or fragment, analog, or peptide thereof is a drug carrier for one or more different additional active agent. In often included embodiments, the additional active agent comprises a benzodiazepine, a penicillin, a methotrexate, a paclitaxel, or a doxorubicin. Also often, the additional active agent comprises a triptan, a dabigatran ethexylate mesylate, or a glucagon-like peptide 1 analog. Medicaments comprising the carrier comprising BSA, or fragment, analog, or peptide thereof, as a carrier for an active pharmaceutical agent (e.g., a chemotherapy agent, anti-rheumatic, antibiotic, etc.) for use in treating or preventing a disease or condition are also contemplated. Also provided are methods of delivering an active pharmaceutical agent for the treatment or prevention of a disease or condition (e.g., cancer, rheumatoid-mediated disease, or infection), comprising administering a carrier comprising a water soluble and/or biodegradable polymer and comprising BSA, or fragment, analog, or peptide thereof as a carrier for an active pharmaceutical agent (such as those mentioned herein).

Also, in certain embodiments, a nanofiber and/or carrier is provided comprising a water soluble and/or biodegradable polymer and glucagon-like peptide 1 or analog, or peptide or fragment thereof. Often in such embodiments, the glucagon-like peptide 1 analog comprises liraglutide, exenatide, lixisenatide, albiglutide, dulaglutide, taspoglutide, and/or semaglutide. Medicaments comprising the carrier comprising glucagon-like peptide 1 or analog, peptide, or fragment thereof for use in treating or preventing a diabetes condition are also contemplated. Also provided are methods of treating or preventing a diabetes condition, comprising administering a carrier comprising a water soluble and/or biodegradable polymer and glucagon-like peptide 1 or analog (such as those mentioned herein), or peptide or fragment thereof.

Also in certain embodiments, a nanofiber and/or carrier is provided comprising a water soluble and/or biodegradable polymer and dabigatran ethexylate mesylate. Often, in certain embodiments, the active agent is incorporated together in the nanofiber or carrier with a taste masking agent or flavoring. Medicaments comprising the carrier comprising dabigatran or analog thereof for use in treating or preventing stroke, deep vein thrombosis, or pulmonary embolism, or another blood clotting condition are also contemplated. Also provided are methods of treating or preventing stroke, deep vein thrombosis, pulmonary embolism, or another blood clotting condition, comprising administering a carrier comprising a water soluble and/or biodegradable polymer and dabigatran or analog thereof.

In frequent embodiments, the polymer solution or carrier further comprises a sodium pump inhibitor an anticonvulsant, an antidepressant, a beta-blocker, a calcium channel blocker, a nonsteroidal anti-inflammatory drug (NSAID), a serotonin receptor antagonist, a serotonin reuptake inhibitor, a serotonin noradrenaline reuptake inhibitor, an analgesic, an antiemetic, an ergot derivative, a neuropeptide antagonist, and/or riboflavin. Such agents are often provided as a combination of active agents in the polymer solution or carrier. Often, the polymer solution or carrier comprises a triptan and an NSAID. In certain embodiments, the polymer solution or carrier comprises a triptan and an antiemetic. In certain embodiments, the polymer solution or carrier comprises a triptan, an NSAID, and an antiemetic.

Often, the nanofibers of the nanofiber protective layer are comprised of a water insoluble polymer.

Also often, an electrospun mucoadhesive layer is deposited on the active layer. Often, the nanofiber mucoadhesive layer in the carrier comprises a polymer, a pH adjusting agent, and a taste masking agent. The polymer in the mucoadhesive layer often comprises a combination of two or more different polymers.

In frequent embodiments, the electrospinning process is a needle-free electrospinning process.

In frequent embodiments, the water soluble and/or biodegradable polymer is comprised of two or more polymers selected from the group consisting of microdispersed oxidized cellulose (mDOC, Loturon), poloxamers (Pluronic), polyvinyl alcohol (PVA), polyethylene oxide (PEO), polylactic acid (PLLA), and polycaprolactone (PCL).

Often, the mucoadhesive layer is comprised of a water soluble and/or biodegradable polymer nanofiber. Also often, the water soluble and/or biodegradable polymer nanofiber is comprised of a polymer selected from the group consisting of chitosan, microdispersed oxidized cellulose derivatives (mDOC, Loturon), Pluronic, PVA, PEO, PLLA, and PCL.

In frequent embodiments, the water soluble and/or biodegradable polymer is comprised of microdispersed oxidized cellulose derivatives (mDOC, Loturon), Pluronic, PVA, PEO, PLLA, and PCL; and the mucoadhesive layer is comprised of chitosan, PVA, and PEO.

In frequent embodiments, the migraine medication comprises rizatriptan benzoate in an amount between about 7 mg to about 44 mg. Often, the migraine medication is included at an active agent total weight of between about 5 mg and 30 mg. Also often, the total carrier weight is between about 23 mg to about 184 mg.

In frequent embodiments, the nanofiber active layer further comprises a non-steroidal anti-inflammatory drug.

In frequent embodiments, a nanofiber protective layer is provided in the carrier. Often, the nanofiber protective layer is comprised of a polymer selected from the group consisting of: (a) a water insoluble polymer or polymer treated to be water insoluble; and (b) two or more of hydroxypropylcellulose (HPC), carboxylmethylcellulose (CMC), polyvinyl alcohol-polyethylene glycol graft copolymer, brand name Kollicoat® IR, PVA, and PEO. Also often, the protective layer is insoluble in saliva and impermeable to saliva and the migraine medication.

The active layer is often soluble in a mouth of a subject within a first time period, and the protective layer is insoluble in the mouth of a subject and impermeable to saliva and the migraine medication. The active layer is also often solubilized within the mouth of the subject within a second time period. In frequent embodiments, the protective layer is permeable to saliva after the second time period. Often, the protective layer is soluble in the mouth of the subject after the second time period. Often, the migraine medication is released from the active layer between the first and second time periods.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION

Figure 1A:
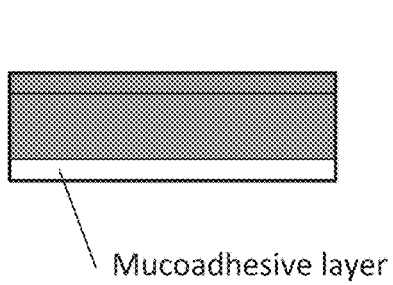
FIGS. 1A and 1B provide diagrammatic representations of a carrier of the present disclosure with and without a mucoadhesive layer.

All patents, applications, published applications and other publications referred to herein are incorporated by reference in their entirety, and/or the specific reasons for which they are cited.

Unless defined otherwise, all technical and scientific terms used herein have the same meaning as is commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. If a definition set forth in this section is contrary to or otherwise inconsistent with a definition set forth in the patents, application, published applications and other publications that are herein incorporated by reference, the definition set forth in this section prevails over the definition that is incorporated herein by reference.

As used herein, "a," "an," or "another" means "at least one" or "one or more."

As used herein, the term "and/or" may mean "and," it may mean "or," it may mean "exclusive-or," it may mean "one," it may mean "some, but not all," it may mean "neither," and/or it may mean "both."

The use of the term "embodiment" means that a particular feature, structure, or characteristic described in connection with the embodiment is included in at least one embodiment of described subject matter. As such, the appearance of the phrases "in one embodiment" or "in an embodiment" throughout the present disclosure is not necessarily referring to the same embodiment. Furthermore, the particular features, structures, or characteristics may be combined in any suitable manner in one or more embodiments.

As used herein, "subject" often refers to an animal, including, but not limited to, a primate (e.g., human). The terms "subject" and "patient" are used interchangeably herein.

As used herein, "treatment" means any manner in which the symptoms of a condition, disorder or disease are ameliorated or otherwise beneficially altered. Treatment also encompasses any pharmaceutical use of the compositions and devices herein.

As used herein, "migraine" refers to a symptom complex occurring periodically and characterized by pain in the head, vertigo, nausea and/or vomiting, photophobia, and/or scintillating appearances of light.

As used herein, the terms "drug" and "active agent" are intended to have overlapping scope and are often used interchangeably and can be organic or inorganic moieties, including polymers such as nucleic acid and/or amino acid containing biopolymers. Often, the active agent comprises an active pharmaceutical ingredient (API).

A "migraine medication," for example, may also be encompassed by the term "drug" or "active agent," which migraine medication may refer to a 5-HT agonist or a triptan, alone or in combination with another 5-HT agonist or triptan, or another medicament such as an NSAID, an antiemetic agent, or another agent such as a polypeptide based migraine medication.

As used herein, "5-HT agonist" and "triptan" are often used interchangably and in the alternative and are intended to have overlapping scope. Triptan refers to the class of triptan molecules. 5-HT agonist refers to agonists of the 5-HT receptor family, including without limitation, 5-HT1D/1B/1F.

As used herein, "polymer solution" refers to a solution for use in an electrospinning process, the polymer solution including an active agent such as a migraine medication.

As used herein, "carrier" or "carrier device" refers to an electrospun nanofiber film comprising multiple layers having varied functionality and an active agent.

As used herein "drug carrier" refers to a substrate (e.g., BSA) used in the process of drug delivery which serves to improve the selectivity, effectiveness, and/or safety of drug administration. For clarity, a "drug carrier" is not intended to have the same meaning or scope as, nor alter the meaning of, a "carrier" or a "carrier device" described herein. As such, a "drug carrier" can serve as or as part of an active agent and incorporated in a nanofiber or "carrier" (or "carrier device") of the present disclosure.

As used herein, "permeation" refers to passage of a substance, agent, or fluid through a membrane, mucosa, or layer. Permeation is often referred to interchangeably with the term "absorption" as it refers to passage of an active agent through oral mucosa such as buccal or sublingual mucosa.

As used herein, "protective layer" refers to a layer that acts as barrier to saliva passage. The protective layer may also be referred to herein as a "barrier layer," "protective side," "impermeable layer" or "impermeable side." In frequent embodiments, the protective layer is present on a single side of the carrier and does not wrap around the carrier to the opposite side of the active layer or to the mucoadhesive layer, for example, to hold carrier layers together.

Nanofibrous carriers according to the present disclosure belong, for example, to the oromucosal mucoadhesive film category of dosage forms intended for sublingual and/or buccal systemic drug administration. Such carriers ensure transmucosal permeation of anti-migraine drugs, alone and/or in combination with therapeutically and chemically-physically compatible drugs of another mechanism of anti-migraine action into systemic circulation of a human subject to treat migraine and/or other types of headache (e.g., premenstrual, menstrual, etc.). Carriers of the present disclosure are usable in human medical and non-human, e.g., veterinary settings.

The nanofibrous carriers of the present disclosure represent a new type of flexible and easily administered oromucosal mucoadhesive medicated preparation. The sublingual and/or buccal route of administration when linked with the nanofiber carriers of the present disclosure, make it possible to deliver either for poorly bioavailable drugs and/or drugs needed for rapid onset of systemic pharmacological action. These carriers provide for, in certain exemplary embodiments, migraine treatment using triptan monotherapy or combination therapy. Moreover, the present carriers provide for co-administration of triptans with other suitable active agents, for example antiemetic agents, using a single carrier preparation (e.g., "two in one" preparation).

Certain embodiments provided herein involve administering an anticoagulant such as dabigatran etexilate mesylate at a low dosage range relative to current dosages, but providing equivalent or increased bioavailability of the administered active agent (relative to the bioavailable active agent when administered via the approved oral route).

In certain embodiments, methods are provided for diabetes treatment. Often, such methods involve administering a glucagon-like peptide 1 analog such as liraglutide in a carrier described herein.

In certain embodiments, methods are provided for delivery of BSA as a carrier for another active agent to a patient. Though BSA is referred to herein as an active agent, this is for efficiency purposes only since its administration is most frequently provided as a drug carrier for an active pharmaceutical agent (API) such as, for example, benzodiazepines, penicillins, methotrexate, paclitaxel, doxorubicin, among many others. Often, such methods involve administering BSA as a drug carrier in a carrier device described herein.

The nanofibrous carriers of the present disclosure are suitable for example, for acute treatment, for patient populations having swallowing difficulties (e.g., uncooperative, nauseated, intubated, or other patients), pediatrics, geriatrics, mentally incapacitated patients, patients with issues related to oral administration such as vomiting and dysphagia, and/or veterinary patient populations.

The present (mucoadhesive) carriers can be characterized as dosage forms that can be attached to a target site onto buccal or sublingual mucosa in the oral cavity to release drug for local delivery and systemic action. Generally, these carriers comprise an active layer that is fully dissolved in mouth cavity. The buccal, and the sublingual mucosa, is well supplied with vascular blood and lymphatic drainage and possess a potentially weak barrier to systemic administration of a certain drugs.

Drug delivery using the presently described carriers that are mucoadhesive preparations, and will not be swallowed, represents an advantageous route for the administration of numerous drugs. The films according to present disclosure further extend, improve and develop electrospinning technology as a medicated carrier intended for systemic administration of active agents such as triptans (also, e.g., BSA, glucagon-like peptide 1, dabigatran, etc.) and/or co-administration of active agents (e.g., for migraine and other headache treatment, and antiemetics such as ondansetron, metoclopramide, etc.).

The main class anti-migraine drugs today comprises selective 5-HT1B/1D agonists (e.g., triptans). Triptans have three main mechanisms of action: cranial vasoconstriction, peripheral trigeminal inhibition, and inhibition of transmission through second order neurons of the trigeminocervical complex (Goadsby, Prog. Neurobiol 62:509-25, (2000)). In addition, lasmiditan (an 5-HT/1F agonist, formally a diptane) is in development and phase III clinical trials and shows promise as another migraine medication contemplated herein. See Reuter et al., Ther Adv Neurol Disord 8(1):46-54 (2015).

5-HT1B/1D agonist compounds are exemplary active agents of the present disclosure, and may be prepared by known processes, for example, those disclosed in U.S. Pat. Nos. 5,290,520, 5,567,819, 5,567,824, 7,279,581, 7,777,049; EP0313397, EP0573221, UK2124210, UK2162522, WO9118897, GB2315673, WO9532197, EP497512, WO06082598, WO07054979, WO06137083; U.S. Pat. Pub No. 20090062550; Chen et al., Tetrahedron Lett. 35:6981-4 (1994); and Street et al., J. Med. Chem. 38:1799-1810 (1995). Triptans as the original active 5-HT1D agonist compounds have been in general use in treatment of migraine since 1993 (sumatriptan). There are seven oral triptans in therapy at present, the examples further include rizatriptan (e.g. rizatriptan benzoate), naratriptan, zolmitriptan, eletriptan, almotriptan, frovatriptan, avitriptan, and donitriptan, including pharmaceutically acceptable salts and esters thereof. These drugs are marketed with various brand names (different by country).

Though not wishing to be bound by any particular theory, 5-HT1B/1D/1F agonists (together referred to herein as 5-HT agonists) have a systemic mechanism of action. For example, 5-HT agonists decrease sensory nerve signaling. In particular, they display high agonist activity, for example, at the serotonin 5-HT1B and 5-HT1D receptor subtypes. 5-HT1B agonists constrict dilated intracranial extracerebral arteries and mechanically reduce the pressure of the vessel, thus decreasing the stimulating signals to the sensory nerves around the vessels. 5-HT1D agonists also decrease the release of vasoactive peptides, which are the messengers in vasodilatation and sterile inflammation. 5-HT1D agonists also lessen the central nociceptive neurotransmission in the trigeminal sensory pathways, thus reducing the impulses sent to ganglions.

As noted, a substantial proportion of patients suffer from severe nausea or vomiting during their migraine attack. This coupled with low oral bioavailability (15%) due to high first-pass metabolism, generally renders oral treatment unsatisfactory. See Dechant K. L, Clissold, S. P. Drugs 43:776-798 (1992). In many cases, sumatriptan efficiency is reduced and with regard to this, the dose necessary to ensure the desired action has to be increased, which leads to an increase in undesirable side effects, patient compliance and at the end, cost of treatment. See Ryan et al., Neurology 49:1225-1230 (1997); Tfelt-Hansen et al., Drugs 60(6): 1259-1287 (2000). The nasal route and subcutaneous route have their own limitations, including variability of onset action and retention time at nasal administration and problems connected with parenteral administration including high prices of self-administration injectable preparations.

The relatively wide group of triptans was developed to increase a likelihood of therapeutic success. The currently available triptans have only minor pharmacodynamic, and somewhat major pharmacokinetic, differences among them. The first meta-analysis of seven oral triptans was published in 2001. See Ferrari et al. Lancet 358:1668-1675 (2001); see also Spierings, Headache 948 (2002); Pascual et al., Headache 47:1152-1168 (2007); Cameron et al., Headache 55 (Suppl 4):221-35 (2015).

In frequent embodiments, rizatriptan (rizatriptan benzoate) is provided as an active agent in the present carrier for administration via the oromucosal sublingual route using a mucoadhesive carrier. Often, the rizatriptan is provided in 5 mg or 10 mg dosages, or 5 mg or 10 mg equivalent dosages. If the migraine returns, a second dose may be administered, for example, 2 hours after the first dose. The maximum daily dose often does not exceed 30 mg in a 24-hour period. For patients receiving propranolol, one example initial dose of rizatriptan is 5 mg, up to an exemplary maximum of 3 doses (15 mg) in 24 hours.

The other active agents based on other mechanisms of action can bring synergic anti-migraine effect and can be enclosed within carriers according to the present disclosure. The different agents may be combined in a layer of the active layer, or in separate layers of the active layer. Drug compatibility or therapeutic urgency often dictates separation of agents into different layers of the active layer to permit varied timing release from the carrier. Manufacturability in the electrospinning process may also affect whether different agents are combined in a polymer solution for electrospinning into a single layer of the carrier.

Moreover, the present carriers provide for direct absorption of substances into systemic circulation without hepatic first-pass effect; and, fast onset of sufficient systemic concentrations of drug. The lag time needed for drug to reach its active places (receptors) within patient body is shorter using the present carriers versus typical oral administration.

The drug delivery properties mentioned above cannot be sufficiently used when the drug is administered oromucosally onto other parts of oral mucosa due to relatively high barrier properties of gingival or palatal mucosa-comparing to very permeable and well vascularized sublingual mucosa. Moreover, the advantageous properties of the sublingual (and/or buccal) route of administration cannot be utilized when a drug is administered but subsequently is washed out by saliva and swallowed into stomach. That fate of drugs is usually connected with the use of fast orodispersible preparations without sufficient mucoadhesivity.

The protective layer is, most frequently, attached to active layer directly and often produced via electrospinning. Often, when in the oral environment, the protective layer is affected in structure when exposed to saliva (or, for example, at a predetermined pH approximately the pH of saliva) to produce a film or gel without permitting access of the saliva to the active layer, or escape of fluid from the active layer through the protective layer. The solubility of protective layer can be controlled. Solubility can range, for example, from delayed solubility (e.g., film or gel structure creation from the electrospun nanofibers with saliva exposure) up to non-soluble forms. The materials forming the protective layer and the pH of the destination environment affect solubility. The protective layer is generally resistant to saliva (limited or not limited by time).

In certain embodiments, the active layer and the protective layer are produced in a single production step. In certain embodiments, the active layer and the protective layer are produced across two or more production steps. In certain embodiments, the protective layer is produced using a coating or spraying system and then contacted or adhered with an active layer. In certain embodiments the active layer is formed on the protective layer. In certain embodiments, the protective layer is formed on the active layer. One or both layers may be formed via electrospinning, as described herein. In frequent embodiments, both layers are produced using an electrospinning process. Key objectives of the protective layer include ensuring maximal concentration gradient of drug, and sufficient time for drug release from the active layer into the mucosa prior to permitting the entry or exit of saliva. In certain embodiments, the protective layer is soluble in the mouth of a subject, but the integrity of the saliva barrier covering the active layer is intact until the active layer has degraded and/or the active agent has been absorbed. In related embodiments, the carrier is ingestible by the subject as or after the protective layer begins to degrade and then permits access of saliva to the active layer or the region where the active layer was present prior to degradation of the active layer.

Though not wishing to be bound by any particular theory, 5-HT1D/1B/1F agonists (together referred to herein as 5HT agonists) have a systemic mechanism of action. For example, the 5-HT agonists decrease sensory nerve signaling. 5-HT1D/1B agonist compounds are within the scope of this disclosure, and may be prepared by known processes, for example, those disclosed in U.S. Pat. Nos. 5,290,520, 5,567,819, 5,567,824, 7,279,581, 7,777,049; EP0313397, EP0573221, UK2124210, UK2162522, WO9118897, GB2315673, WO9532197, EP497512, WO06082598, WO07054979, WO06137083; U.S. Pat. Pub No.

20090062550; Chen et al., Tetrahedron Lett. 35:6981-4 (1994); and Street et al., J. Med. Chem. 38:1799-1810 (1995). Examples of the 5-HT1D/1B compounds useful in this method of treatment and this formulation include sumatriptan, rizatriptan (rizatriptan benzoate), naratriptan, zolmitriptan, eletriptan, almotriptan, frovatriptan, avitriptan, and donitriptan, including pharmaceutically acceptable salts and esters thereof. Lasmiditan is an example of a 5HT1F compound also useful in migraine treatment. Rizatriptan benzoate is known by the chemical name, N,N-dimethyl-5-(1H-1,2,4-triazol-1-ylmethyl)-1H-indole-3-ethanamine benzoate. Rizatriptan benzoate is a selective 5-HT receptor agonist, and is marketed as an oral formulation for acute treatment of migraine.

In certain embodiments, the sulfate salt of rizatriptan (e.g., N,N-dimethyl-2-[5-(1,2,4-triazol-1-yl-methyl)-1H-indol-3-yl]ethylamine) is used as the 5-HT agonist, and dosage provided in the carrier at about 0.01 mg to about 100 mg rizatriptan benzoate. Often, the drug is provided at about 0.1 to about 30 mg. Also often, the drug is provided at about 1 mg to about 15 mg, or about 5 mg to about 10 mg. Extended release of the drug from the nanofiber layers may be provided when the drug is provided at maximum daily-dosage level concentrations. Rizatriptan benzoate oral administration has historically been intended for the acute treatment of migraine with or without aura in adult patients. The recommended starting dose of rizatriptan is 5 mg or 10 mg. If the migraine returns, a second dose may be administered 2 hours after the first dose. The maximum daily dose, in general, should not exceed 30 mg in a 24-hour period. For patients receiving propranolol, the initial dose of rizatriptan is 5 mg, up to a maximum of 3 doses (15 mg) in 24 hours. The safety and efficacy of treating more than 4 headaches in a 30-day period has not been established.

Overall, the inventors have provided formulations and carriers herein that address multiple needs in the art. In particular, the presently described carriers comprise medicated preparations characterized by, for example in the area of migraine, a faster and/or stronger onset of an anti-migraine effect than existing drugs or delivery systems. Safer administration of anti-migraine drugs at the appropriate dosage has also been provided with the present carriers and formulations, such that over-dosing to overcome the low bioavailability issue of current oral, nasal, and pulmonary drugs is not necessary. Moreover, carriers are provided herein that may be safely and effectively administered to a subject afflicted with a migraine characterized by nausea and vomiting. In view of these benefits, improved patient compliance with migraine treatment or management protocols is possible.

In a frequent embodiment, the triptan active agent incorporated in the carrier is selected from the group consisting of rizatriptan, naratriptan, zolmitriptan, eletriptan, almotriptan, frovatriptan, avitriptan, and donitriptan.

Also frequently, the active agent comprises a small or a large molecule moiety. For example, in certain embodiments the active agent comprises a biopolymer such as a polypeptide, a protein, a nucleic acid, a polysaccharide, a peptide, a carbohydrate, DNA, RNA, or a lipid. In certain embodiments, active agent polymers of up to about 67 kDa or 70 kDa are provided. Also, in certain embodiments, the active agent is selected from a group comprising a triptan, BSA, a glucagon-like peptide 1, or dabigatran.

Devices

A variety of carriers may be employed for active agent (e.g., sublingual triptan or other 5-HT agonist, BSA, glucagon-like peptide 1, dabigatran, etc.) delivery according to the presently described methods, materials, and devices. Nanofibrous layers containing an active agent such as a triptan or another 5-HT agonist (also, e.g., BSA, glucagon-like peptide 1, dabigatran, etc.), carrier, buffer, and/or other biocompatible and physiologically inactive or active substance often form at least a portion of the carriers of the present disclosure. A variety of excipients, including mixtures thereof, are often used to ensure all needed properties of a final product are employed for active agent such as sublingual triptan or other 5-HT agonist (also, e.g., BSA, glucagon-like peptide 1, dabigatran, etc.) delivery. In the present carriers, a complex polymeric matrix is used as a drug release platform that may be composed of several components in order to achieve well-designed drug delivery profile, mucoadhesivity and solubility, and, the present carriers usually utilize hydrophilic polymers as an active layer (or excipient core).

The polymers are not mostly used alone, however a mixture of them is often utilized to obtain optimal processability, electrospinability and optimal properties of a final product. From the other view is clear that one excipient possesses several different and important properties, the relationships among concentration, solubility in liquids, imbibition, wettability, viscosity, conductivity, dissociation, mutual miscibility and other properties of a given type of polymer is usually typical and makes possible to use it in several quite different functions.

Nanofibrous layers of the carriers containing an active agent such as triptan or other 5-HT agonist (also, e.g., BSA, glucagon-like peptide 1, dabigatran, etc.), excipients, buffer, and/or other biocompatible and physiologically inactive or active agents often form at least a portion of the (the dosage forms, the final product) carriers of the present disclosure. In certain embodiments a rizatriptan benzoate preparation is composed of two or more nanofiber layers with adjustable drug release profiles. Each of these layers is provided with nanofibers having a fiber average diameter of less than about 550 nm. Most frequently, the fiber diameter is less than 400 nm, or between about 50 nm to about 400 nm.

Needle free (also known as nozzle-less or needleless) electrospinning, for example roller electrospinning, is utilized in frequent embodiments to produce the nanofibers of the present disclosure. For example, electrospinning equipment available from Elmarco Ltd. (e.g., NANOSPIDER®; Liberec, Czech Republic) is often used to produce the requisite nanofiber layers. The nanofibers are produced using an electrospinning process using a solution of polymer together with drug and all other components. NANOSPIDER® technology is an electrospinning process that is needle-free, uses high voltage, and process from a free liquid surface. See, e.g., U.S. Patent App. Pub. No. 2012177767, WO2012139533 (A1), EP2565302 (B1). The technology is based upon a polymer solution or polymer melt, where after high voltage application, Taylor cones are created from a thin polymer film and further nanofibers are produced. The entire process is performed at high voltage and Taylor cones/nanofibers are formed between collecting and spinning electrodes. Many types of polymers with wide range of molecular weights and polymer salts or derivatives can be dissolved in various known solvents (depend on polymer solubility) and utilized to form nanofibers in this process. Recent NANOSPIDER® technology uses an endless motion wire system, where a wire is wetted by a thin film of polymeric solution that is smoothly delivered on the wire by specific motion of the spinning head. Here the thickness of the polymer film is often controlled by using slits chosen according to the polymer solution viscosity. These electrospinning technologies are considered to be environmental-friendly, for example, due to the mainly aqueous solvents and water-miscible co-solvents used in such processes.

In certain embodiments, a protective layer and an active layer are provided. An active layer generally incorporates an active agent such as 5-HT agonist or triptan (also, e.g., BSA, glucagon-like peptide 1, dabigatran, etc.). Though not wishing to be bound by any specific theory of operation, the protective layer provides a barrier between an active layer and the environment in the mouth of a subject. One important factor in oral absorbable drugs is the action of saliva on either or both the active agent or washing away the active agent with swallowing of it into a distal part of gastrointestinal tract without passing through the mucosal membrane. If a medicated preparation is soluble or dispersible in the mouth, then swallowing of saliva with anything containing active drug displaces the drug from the mouth mucosal absorption surfaces to the stomach. This circumstance is responsible for a paradoxical result in the delay of the onset of the drug effect when sublingual orodispersible tablets are used instead of classical tablets. The same results can be logically expected with the use of any oromucosal preparation that is dispersible or soluble in the mouth saliva but not fixed for a certain minimal time onto mucosal absorption surface. These problems of oromucosal drug administration have been addressed with the presently described carriers and their use. As further described herein, the present carriers address this, for example, through the use of a protective layer to prohibit saliva from penetrating into, and/or carried drug escaping from, an active layer containing incorporated active agent such as 5-HT agonist or triptan (also, e.g., BSA, glucagon-like peptide 1, dabigatran, etc.). Drugs present in an active layer in the present carriers, when placed in the mouth of a subject and in contact with the mucosal substance (e.g., especially sublingual mucosa), penetrate through the epithelium and are delivered into systemic circulation of the subject, thus avoiding the hepatic first-pass effect on the drug. See, e.g., Rowland, M et al., *J. Pharm. Sci.* 61 (1): 70-74 (1972); Pond, S. M. & Tozer, T. M., *Clin. Pharmacokinetics* 9 (1):1-25 (1984).

Pharmaceutically acceptable polymers and/or their derivatives are generally preferred to form the layers of the presently described carriers. Polymer derivatives refer to polymers with varied molecular weight or modification of functional groups, including co-polymers, cross-polymers, or combinations thereof. Such polymers may be commercially available, or can be prepared using known techniques.

Hydrophilic polymers include, for example, some of the following polymers including their derivatives and salts: polyethylene glycols (PEGs), polyethylene oxides (PEOs), copolymers of polyethylene oxide with other alkylene oxides, particularly as block copolymers of PEG and polypropylene oxide or polybutylene oxide, polyvinyl alcohol, polyvinyl pyrrolidones (PVPs), albumin, dextran, hyaluronic acid, alginates, carrageenan, chitosan, gelatin, collagen, zein, and derivatives, polyacrylic acid, cellulose derivatives such as carboxymethyl cellulose sodium, hydroxyethyl cellulose (HEC), hydroxypropylcellulose (HPC), hydroxypropylmethyl cellulose (HPMC), hydroxypropylmethyl cellulose phthalate, cellulose acetate phthalate, oxidized cellulose (e.g., in microdispersed form). Hydrophilic polymers are generally water soluble polymers.

Hydrophobic polymers include, for example, some of the following polymers including their derivatives and salts: Cellulose derivatives (acetylcellulose, methyl cellulose, ethylcellulose, noncrystalline cellulose); polymers based on (meth)acrylates (i.e., acrylates, methacrylates, alkylacrylates and copolymers thereof), including (meth)acrylic acid, (meth)acrylamides, hydroxyethyl (meth)acrylates; poly(alpha-hydroxy acids) and its copolymers such as poly(c-caprolactone), poly(lactide-co-glycolide), poly(alpha-aminoacids) and its copolymers; polyurethanes (all with approval for usage in medical/pharmaceutical field). In certain embodiments, hydrophilic polymers are treated to have hydrophobic properties and/or become water insoluble or partially water insoluble, for example when utilized in the protective layer.

Biodegradable polymers may include certain hydrophilic or hydrophobic polymers, but often have certain hydrophobic properties. Some exemplary biodegradable polymers include polycaprolactone, polylactic acid, poly(lactide-co-glycolide), polyglycolic acid, among others.

An active layer, protective layer, or mucoadhesive layer (and solutions utilized to prepare such layers) may comprise a mixture of polymers, including water soluble or hydrophilic polymers and water insoluble, hydrophobic polymers or biodegradable polymers together in the layer or solution. Often the primary constituent polymer type for each layer (or solution the layer is prepared therefrom) is discussed herein, though not to the exclusion of other polymers.

At least one active layer is often provided with a wetting agent and/or penetration enhancer such as: an anionic surfactant (e.g. sodium laurate, sodium lauryl sulfate, sodium dodecyl sulfate, dioctyl sodium sulfosuccinate, sodium glycocholate), a non-ionic surfactant (polysorbates, nonylphenoxypolyoxyethylene, polyoxyalkylene, polyoxyethylene alkyl derivatives), or a cationic surfactants (cetylpyridinium chlorid, poly-L-arginine); fatty acids and derivatives (such as oleic acid, lauric acid, linoleic acid), acetylcholines, acylcarnitine, monoglycerides, diglycerides and triglycerides, and/or caprylic acid; sulfoxides (such as dimethyl sulfoxide, and/or dodecyl sulfoxide); alcohols (including ethanol, isopropanol, propylene glycol, glycerol, propanediol) and/or menthol; chelating agents such as EDTA, citric acid, and/or salicylates; bile salts and derivatives and others compounds such as cyclodextrins, polyvinyl pyrrolidone, lactose, triacetin, and/or menthol. In certain embodiments, hydrophilic polymers are treated to have hydrophobic properties and/or become water insoluble or partially water insoluble.

At least one layer is often provided with a taste masking compound. Exemplary taste masking agents often include a sweetener or flavouring compound, e.g., sucralose, erythritol, isomaltitol, D-maltitol, lactitol, D-mannitol, neotame, saccharin, dextrose, sorbitol, xylitol, rebaudioside A, and/or thaumatin, D-limonene, L-linalol, nerol, citral, citronellyl formate, anisil alcohol, anisyl formate, isoamyl salicylate, isobutyl anthranilate, isopropyl valerate, linalyl anthranilate, methyl ionone, menthol, thymol, and/or eugenol.

At least one layer is often provided with least one layer containing a pigment or dye that has a distinctive color. The coloration is often provided to easily distinguish a two-sided carrier, with a first side having one color (or white), and a second side having a different color (or white if the first side is not white). The first and second sides referring to active and protective sides, respectively, to ease proper placement of the carrier in the oral cavity by a subject, user, or health care professional. In an exemplary embodiment, a first side having a distinctive coloration is identified as an active side of the carrier intended to be placed directly in contact with the biology of the oral cavity. In another exemplary embodiment, a second side having a distinctive coloration is identified as a protective side of the carrier intended to face an opening of the oral cavity or otherwise not be adhered to the biology of the oral cavity. On one embodiment, the protective layer or side is blue and the active side or layer is white. The dye or pigment is generally biocompatible and may be incorporated in the polymer solution and formed with the nanofibers, for example, in an electrospinning process. Exemplary dyes or pigments can be used alone or in mixtures used for coating or dyeing systems approved for usage in food or pharmaceutical industry.

In certain embodiments, the taste masking agent and penetration agent are provided in the same layer. In related embodiments, the taste masking agent is often provided in the active layer and/or the mucoadhesive layer. Also in related embodiments, the penetration agent is often provided in the active layer and/or the mucoadhesive layer.

Figure 1B:
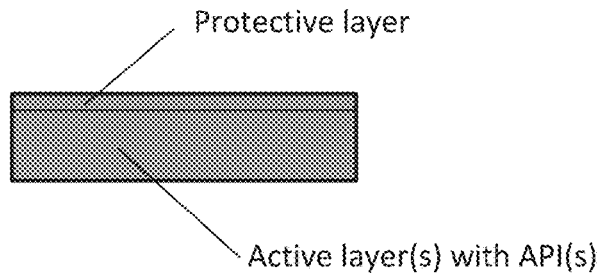

In certain embodiments, the first and second sides are provided, each having a different tactile feel to permit a subject to determine which side is the active side and which side is the protective layer without having to directly view the carrier. Bumps, weave patterns, textile types, imprints, coatings, adherence agents, among other options, may be employed to provide the desired difference in tactile feel between the first and second sides. FIGS. 1A and 1B represent side views of an exemplary carrier, including two or three layers, though lacking a rim. Specifically, FIG. 1A provides a carrier having three layers including a protective layer, an active layer including a active agent such as a 5-HT agonist or triptan, and a mucoadhesive layer (also, e.g., BSA, glucagon-like peptide 1, dabigatran, etc.). FIG. 1B provides a view similar to FIG. 1A, though the carrier lacks the mucoadhesive layer. Though the active layer is depicted as thicker than either or both the protective and mucoadhesive layers in FIGS. 1A and 1B, this relative thickness is merely representative and is not intended to be limiting. This thickness may vary based on the desired application, amount or number of layers of nanofibers that have been laid down, type and amount of physiologically active agent, and/or manner of depositing the physiologically active substance on the active layer, or other factors.

The present carriers are most frequently employed without a rim (e.g., fixation rim) comprising an overlap of a protective layer or impermeable layer material on the active side of the carrier. As such, in one embodiment the carrier does not comprising a protective layer rim on the same side of the carrier as the active side.

Mucoadhesive layers interact with the mucus layer in the oral cavity, covering the mucosal epithelial surface and mucin molecules to, for example, increase the residence time of the active agent dosage at the site of placement. As used herein, the term "mucoadhesive layer" refers to an environment capable of allowing passage of a drug contemplated medicament to a mucosal surface. This layer is often formed of any of a variety of substances. For example, polysaccharides (e.g., chitosan pectin, hyaluronic acid, etc) alone or together with other mucoadhesive polymers such as microdispersed oxidized cellulose derivatives, carbopols, polyacrylic acids, among others. In certain embodiments, the mucoadhesive layer is a first contact layer that covers the active layer using thinly spun or a thin layer of nanofibers made of suitable mucoadhesive polymers mentioned above. The mucoadhesive layer is often a bioerodable/biodegradable or water soluble mucoadhesive layer.

Nanofiber formation is often provided on a textile backing material that becomes, forms, or contains the protective layer. The textile backing material may be coated or lined with a protective layer, wherein the textile is removed after nanofiber formation to reveal the protective layer. In certain embodiments, fibers are grown on the textile backing through the use of electrospinning using techniques described herein. Polymer solutions are often tested for viscosity and consistency prior to electrospinning to ensure optimal fiber consistency within one or more predefined parameters. Consistency in nanofiber formation has been found to be important to permit predictable active agent loading and release, and often a reduction of residual active agent in the carrier after the carrier is utilized as directed. The speed of the textile feed during the electrospinning process is often varied to affect nanofiber deposition and nanofiber layer thickness.

In one embodiment, a rizatriptan benzoate containing active layer is provided through electrospinning, utilizing the following exemplary parameters: a wire electrode distance of 180 mm; a relative humidity inlet of between about 27-31% and a temperature of between about 21-24.5° C.; a relative humidity outlet of between about 26-32% and a temperature of between about 21-24.5° C.; a voltage of about 61.6/−18 kV (current 0.2-0.3 mA). In such an embodiment, a polypropylene spunbond is provided at an exemplary speed of about 21 mm/min. The polymer solution in such an embodiment is often at a viscosity of about 462±46 mPa·s at 22° C., and a conductivity of about 2190±210 μS/cm at 22° C.

The presently devised electrospinning conditions and materials have been identified as being useful to prepare nanofiber layers that are capable of reliably and reproducibly holding a pre-determined quantity of active agent (e.g., triptan, BSA, glucagon-like peptide 1, dabigatran, etc.), which provides tightly-controlled dosing parameters. The carrier need not be overloaded with active agent during formation, thus avoiding production losses and active agent coming out of solution when being incorporated in the carrier. The resulting nanofibrous carriers have other beneficial properties not previously seen, for example in oromucosal dosing schemes and devices. For example, the well-documented problem of residual active agent in the carrier after use is essentially not present in many embodiments of the carriers of the present disclosure.

Though not wishing to be bound by any particular theory, active agent is thoroughly released from the active layer when the carrier is used as directed in the oral cavity of a subject. The evenly distributed nanofiber layers both consistently hold and consistently release entrained active agent. Nanofiber diameter and/or length in the carrier has been developed to aid such consistency. This even distribution of the nanofibers within the nanofiber layers of the carrier also permits a degree of structurally-intact flexibility in the nanofiber layers that is previously unseen in oromucosal devices. Such flexibility aids placement of the carrier and permitting the carrier to be held or adhered in the proper oral mucosa location for the requisite period of time to permit active agent release. Also, in the case of migraine patients in the midst of a migraine attack, the ease of placement is enormously beneficial in both therapeutic effect and compliance with recommended dosing parameters.

Drug Release Kinetics

Kinetics of the carriers of the present disclosure can be tightly controlled over a desired range by adjusting one or more factors in carrier formation. For example, the manner of nanofiber formation, polymer solution constituents and consistency, pH variations, speed of textile, voltage and current, thickness of active layer, gelling property variations, drug that is utilized, wettability variations, nanofiber diameter variations, mucoadhesive layer choices, active agent loading, among other variations. For example, for a quick release of active agent, polymers are often utilized that are quickly dissolved at a desired pH value (e.g., the pH in saliva) such as cellulose derivatives soluble in water, including HPMC, Ca2+ or Na+ salts of microdispersed oxidized cellulose as well as PVP, PVA in mixture with PEO, among others. To achieve a more extended release profile, polymers forming the active layer are selected that begin to gel at a desired pH, which may be different than the typical pH of saliva, using for example, CMC Na salts, pH sensitive carbomers (carbopols), polycarbophiles, pectins or crosslinked polymers whose noncrosslinked form is swellable, among other options. The inventors have determined that pH variations have a large impact on polymer dissolution. The inventors have also determined means for adjusting the pH dissolution value for the polymer system (i.e., active layer) close to an intended pH value.

For example, in certain embodiments, pH is adjusted to close to an intended pH value using a selection of specific polymer types or mixtures that have desired pH dissolution characteristics, including the use of HPC, which is typically soluble in water, but at high pH value is insoluble. A carrier having multiple nanofiber layers that respond to a pH cascade, where each layer is adjusted to have a specific, and often different, dissolution characteristic at a desired pH to control drug release over time and in specific conditions. For example, in one embodiment, the mucoadhesive layer has a low dissociation pH for mucus removal, and layers of the active layer dissolve at higher pH values (e.g., at or around a typical pH for saliva or another pH value that optimized bioavailability of the drug). In related embodiments, the protective layer is provided with the highest pH value of the materials or layers of the carrier to withstand (i.e., remain intact and undissolved) extended contact with saliva.

The thickness of the active layer may also be varied to adjust the amount of active agent (i.e., 5-HT agonist or triptan, BSA, glucagon-like peptide 1, dabigatran, etc.) within the active layer. Though not intending to be bound by any particular theory, varying the thickness of the active layer permits a corresponding varying of active agent that can be incorporated, for example, prior to supersaturation of the medium and/or having the active agent come out of solution during active agent loading. The diameter of the fibers in the nanofiber active layer may be varied in certain embodiments. Also often, the thickness of the active layer is adjusted by including more or fewer nanofiber layers using, for example, electrospinning methods described and contemplated herein. For example, in one embodiment a single nanofiber layer comprising an active agent is provided. Often, two nanofiber layers comprising an active agent are provided, together forming the active layer. In certain embodiments, three to eight nanofiber layers comprising an active agent are provided, together forming the active layer. In certain embodiments, two or more nanofiber layers comprising an active agent are provided, together forming the active layer.

When referred to herein, a nanofiber layer may refer to the output of a single head/wire, or the output of multiple heads/wires working in unison. A nanofiber layer is meant herein to refer to a layer produced in a single production cycle, rather than the positioning of a layer having single nanofiber in thickness. In practice, each production cycle provides a mesh of overlapping nanofibers on a substrate such as a textile. Multiple nanofiber layers, produced in multiple production cycles often comprise the active layer.

The number of layers of each layer of the carrier depends on the electrospinning technology that is utilized. In frequent embodiments two layers with drug are provided in the active layer of the carrier, which enhances homogeneity. Often, however, a single nanofiber layer comprising with drug in the active layer is provided in the present carriers. In general, however, there is no limit in numbers of layers.

The active agent loading refers to a ratio of drug to the weight of the carrier system (e.g., whole dry matter content excluding solvents). The inventors have discovered that it is often important to monitor active agent loading since the choice of loading concentrations has an effect on production costs, material or active agent losses, and uniformity or consistency of the active agent in the carrier. Active agent loading procedures and concentrations depends, for example, on the active agent itself. For example, the solubility of the active agent within a specific solvent system has an effect on the loading procedure, conditions, or materials. Under certain solvent systems the active agent may be fully or partially dissolved; partial dissolution often complicates loading. The choice of active layer polymer material (comprising the nanofibers) also often affects loading.

A variety of parameters are evaluated and adjusted when producing nanofibers comprising active agent according to the present methods as each polymer has distinctive behaviour during the electrospinning process that must be optimized to provide the carriers of the present disclosure. In particular, the carriers of the present disclosure comprise a uniform nanofiber diameter (e.g., 400 nm or less, or between about 200 nm to about 400 nm) and uniform deposition positioning that permits predictable dissolution characteristics and active agent release.

For example, different polymers have different molecular weights, ranging from a few hundreds of daltons up to several million daltons. The molecular weight and the solvent utilized to dissolve the polymer are closely connected with viscosity. Though not wishing to be bound by any particular theory, each polymer has a different viscosity curve that depends, at least in part, on its primary and secondary chemical structure, the type of polymer (e.g. alternating co-polymer), degree of polymerization, its substitutions, solvents being utilized, means of mixing, among other factors. In frequent embodiments as described herein, polymers comprising an active agent or combination of active agents having molecular weights up to about 70 kD are specifically contemplated herein for integration and use in the carriers of the present disclosure.

In particular, a high resulting viscosity usually provides relatively thinner nanofibers versus low viscosity or very diluted polymeric solutions. Very diluted solution also provides decreased drug release kinetic prediction due to the presence of defects and reduced uniformity. High viscosity solutions also often provide a decreased yield or production capability compared with lower viscosity solutions. The surface tension of the solution is also connected with the electrospinning process in that it affects the propensity of the solution to create Taylor cones, and a surfactant is often utilized to adapt the surface tension of the solution to provide a desired surface tension. In certain embodiments, the viscosity of a polymer solution for electrospinning of a protective layer, active layer, or mucoadhesive layer is equivalent in (SI) units to one of the exemplary polymer solutions described herein.

The conductivity of the electrospinning solution is also an important factor, because non- or low conductive solutions are more complicated to subject to electrospinning or may not be capable of electrospinning compared with solutions that are more conductive. Highly conductive polymer solutions are often preferred for producing the active layer of the present carriers. Salts are often utilized to increase conductivity to a degree. When salts are heavily incorporated, they may have an effect on the release of the active agent and the bioavailability of the active agent when administered. The pH value of the solution is also often closely related to active agent bioavailability. With regard to the protective layer, the pH is selected according to its solubility after the contact with saliva/mucosa.

At a defined pH, an active agent may have a bioavailability that will stay the same, increase or decrease with a changing pH. Often, the pH for optimal bioavailability of the active agent comprised in the nanofiber is known. pH adjusting agents are often utilized to provide a desired solution pH. A pH adjusting agent, as used herein, refers to any acidic or any basic agent that does not alter the physicochemical nature of the active agent. This agent (including multiple different agents) is often selected from sodium hydroxide (NaOH), kalium hydroxide (KOH), a sodium (bi)carbonate, a mono- or disodium phosphate, triethanolamine, citric acid, lactic acid, acetic acid, ascorbic acid, malic acid, gluconic acid, glutamic acid, hydrochloric acid, sulfuric acid, phosphoric acid, succinic acid, tartaric acid, butyric acid, arginine hydrochloride, and creatinine. Preferably, the pH of the formulation according to the present disclosure is between 4.0 and 9.0.

Therefore, most frequently, the choice of the polymer used to generate the nanofibers for the carrier is varied based on the active agent and desired drug release profile. Optimal pharmacokinetics and release speed or conditions (e.g., release at a specific pH level) are often tailored to suit the therapeutic application according to the present methods to adapt the speed and total dosage delivery of active agent. In certain embodiments, the drug loading is optimized immediately below supersaturation.

When loading the active agent, it is often deposited directly on, or situated in the space between, the nanofibers in the active layer or carrier. Coating, sinking, or encapsulation by coaxial and emulsion electrospinning are frequent methods utilized to produce the nanofibers, nanofiber layers, and/or carriers of the present disclosure. A solution or other dispersion are often utilized to deposit the active agent. In certain embodiments, active layer or carrier loading with active agent is accomplished according to methods set forth in U.S. Patent App. Pub. No. 20130323296.

The electrospinning methods described herein are useful to prepare nanofibers comprising a variety of active agents having a variety of molecular weights. Both small and large molecules—chemical moieties, peptides, polypeptides, proteins, saccharides, polysaccharides, among others, are contemplated as active agents herein. For example, the active agent may comprise up to about a 750 kDa molecule. In oromucosal preparations, often the active agent is often about or less than about 66 kDa, 67 kDa, or 70 kDa.

Combined Administration

In some embodiments, the migraine drug (e.g., 5-HT 1/B, 1/D, 1/F agonist) is administered in combination with one or more other anti-migraine agent, antiemetic agent, and/or other agent. Other combinations are also described herein. As used herein, the term "anti-migraine agent" includes any pharmacological agent which may be used to treat or prevent migraine attacks (i.e., any pharmacological agent which may be used for the treatment or prevention of migraine). For example, a triptan can be administered in combination with any of the following: a sodium pump inhibitor an anticonvulsant, an antidepressant (e.g., amitriptyline, nortriptyline, desipramine, etc.), a beta-blocker, a calcium channel blocker, a nonsteroidal anti-inflammatory drug (NSAID), a serotonin receptor antagonist, a serotonin reuptake inhibitor, a serotonin noradrenaline reuptake inhibitor, an analgesic, an antiemetic, an ergot derivative, a neuropeptide antagonist, and/or riboflavin.

Exemplary NSAIDs may include nabumetone, naproxen, naproxen sodium, tolmetin sodium, valdecoxib, and/or combinations thereof.

In one embodiment, the carrier is provided comprising rizatriptan and an NSAID. The active layer is often formulated in such embodiments with different or distinct nanofiber layers or portions comprising the rizatriptan agent or the NSAID agent. In certain embodiments, the rizatriptan and the NSAID are comprised in the same nanofiber layer of the active layer.

Other features and advantages of the disclosure will be apparent from the following detailed description, and from the claims.

The present disclosure is further described by the following exemplary embodiments. The embodiments are provided solely to illustrate the disclosure. These exemplifications, while illustrating certain specific aspects of the disclosure, do not portray the limitations or circumscribe the scope of the disclosure.

In one embodiment, a protective layer was formed via electrospinning using methods and conditions, for example, as set forth herein above, using the materials set forth below:

a) counted as wt % in prepared solution:

| | |
|---|---|
| Polymer | 5.35 wt % |
| Hydrophobic polymer | 1.13 wt % |
| Wetting agent | 0.61 wt % |
| pH adjusting agent | 0.33 wt % |
| Water | 90.12 wt % | b) Dry matter content:

| | |
|---|---|
| Polymer | 96.44 wt % |
| pH adjusting agent | 3.56 wt % |

In one embodiment, an active layer containing rizatriptan benzoate was formed via electrospinning using methods and conditions, for example, as set forth herein above, using the materials set forth below:

a) counted as wt % in prepared solution:

| | |
|---|---|
| Polymer | 9.00 wt % |
| Wetting agent/penetration enhancer | 3.93 wt % |
| Taste masking compound | 0.36 wt % |
| Active agent | 4.31 wt % |
| Water | 82.4 wt % | b) Dry matter content:

| | |
|---|---|
| Polymer | 65.86 wt % |
| Taste masking compound | 2.63 wt % |
| Active agent | 31.51 wt % |

In one embodiment, an active layer containing rizatriptan benzoate was formed via electrospinning using methods and conditions, for example, as set forth herein above, using the materials set forth below:

a) counted as wt % in prepared solution:

| | |
|---|---|
| Polymer | 10.17 wt % |
| Wetting agent/penetration enhancer | 1.31 wt % |
| Taste masking compound | 0.10 wt % |
| Active agent | 3.78 wt % |
| Water | 84.64 wt % | b) Dry matter content:

| | |
|---|---|
| Polymer | 72.34 wt % |
| Wetting agent/penetration enhancer | 1.31 wt % |
| Taste masking compound | 0.73 wt % |
| Active agent | 26.93 wt % |

In one embodiment, an active layer containing rizatriptan benzoate was formed via electrospinning using methods and conditions, for example, as set forth herein above, using the materials set forth below:

a) counted as wt % in prepared solution:

| | |
|---|---|
| Polymer | 9.25 wt % |
| Wetting agent/penetration enhancer | 1.19 wt % |
| pH adjusting agent | 1.70 wt % |
| Taste masking compound | 0.09 wt % |
| Active agent | 3.44 wt % |
| Water | 84.33 wt % | b) Dry matter content:

| | |
|---|---|
| Polymer | 63.82 wt % |
| Wetting agent/penetration enhancer | 1.19 wt % |
| pH adjusting agent | 11.79 wt % |
| Taste masking compound | 0.64 wt % |
| Active agent | 23.75 wt % |

With regard to the active layer formation examples above, the content of rizatriptan benzoate can be controlled by adjusting or controlling a thickness of nanofiber layer in addition to controlling loading of the rizatriptan benzoate. Active agent precipitation is less desired and therefore careful control of loading is provided by controlling such that overloading the solution with the active agent has been monitored. Thus, often the content of the active agent is controlled by varying the thickness of the active layer, including by adjusting the number of nanofiber layers in the active layer. As explained in further details herein, drug release and delivery kinetics has been, and can be, controlled by many adjusting parameters such as polymer solution composition (e.g., choice of polymers and their respective pH dissolution characteristics, gelling properties, wettability, layer thickness, nanofiber diameter, active agent content, among other parameters.

The content of rizatriptan in the carrier often varies according to required dosage in one strip. In one embodiment, a carrier containing 5 mg rizatriptan (+/−15%) has been produced. In such an embodiment, 7.27 mg rizatriptan benzoate salt is used as the amount of starting active agent. In a related embodiment, the carrier containing 5 mg rizatriptan weighs between about 23 mg to about 31 mg. An NSAID agent is incorporated in such carriers in certain embodiments.

In one embodiment, a carrier containing 6 mg rizatriptan (+/−15%) is produced. In such an embodiment, 8.72 mg rizatriptan benzoate salt is used as the amount of starting active agent. In a related embodiment, the carrier containing 6 mg rizatriptan weighs between about 27 mg to about 37 mg. An NSAID agent is incorporated in such carriers in certain embodiments.

In one embodiment, a carrier containing 7 mg rizatriptan (+/−15%) is produced. In such an embodiment, 10.18 mg rizatriptan benzoate salt is used as the amount of starting active agent. In a related embodiment, the carrier containing 7 mg rizatriptan weighs between about 32 mg to about 43 mg. An NSAID agent is incorporated in such carriers in certain embodiments.

In one embodiment, a carrier containing 8 mg rizatriptan (+/−15%) is produced. In such an embodiment, 11.63 mg rizatriptan benzoate salt is used as the amount of starting active agent. In a related embodiment, the carrier containing 8 mg rizatriptan weighs between about 36 mg to about 49 mg. An NSAID agent is incorporated in such carriers in certain embodiments.

In one embodiment, a carrier containing 9 mg rizatriptan (+/−15%) has been produced. In such an embodiment, 13.09 mg rizatriptan benzoate salt is used as the amount of starting active agent. In a related embodiment, the carrier containing 9 mg rizatriptan weighs between about 41 mg to about 56 mg. An NSAID agent is incorporated in such carriers in certain embodiments.

In one embodiment, a carrier containing 10 mg rizatriptan (+/−15%) is produced. In such an embodiment, 14.53 mg rizatriptan benzoate salt is used as the amount of starting active agent. In a related embodiment, the carrier containing 10 mg rizatriptan weighs between about 46 mg to about 62 mg. An NSAID agent is incorporated in such carriers in certain embodiments.

In one embodiment, a carrier containing 15 mg rizatriptan (+/−15%) is produced. In such an embodiment, 21.81 mg rizatriptan benzoate salt is used as the amount of starting active agent. In a related embodiment, the carrier containing 15 mg rizatriptan weighs between about 69 mg to about 92 mg. An NSAID agent is incorporated in such carriers in certain embodiments.

In one embodiment, a carrier containing 20 mg rizatriptan (+/−15%) is produced. In such an embodiment, 29.07 mg rizatriptan benzoate salt is used as the amount of starting active agent. In a related embodiment, the carrier containing 20 mg rizatriptan weighs between about 92 mg to about 123 mg. An NSAID agent is incorporated in such carriers in certain embodiments.

In one embodiment, a carrier containing 30 mg rizatriptan (+/−15%) is produced. In such an embodiment, 43.61 mg rizatriptan benzoate salt is used as the amount of starting active agent. In a related embodiment, the carrier containing 30 mg rizatriptan weighs between about 138 mg to about 184 mg. An NSAID agent is incorporated in such carriers in certain embodiments.

In one embodiment, a mucoadhesive is prepared using methods and conditions, for example, as set forth herein above, using the materials set forth below:

a) counted as wt % in prepared solution:

| | |
|---|---|
| Polymer | 10.02 wt % |
| pH adjusting agent | 7.81 wt % |
| Taste masking compound | 0.31 wt % |
| Water | 81.86 wt % | b) Dry matter content:

| | |
|---|---|
| Polymer | 83.20 wt % |
| pH adjusting agent | 14.22 wt % |
| Taste masking compound | 2.58 wt % |

Carriers have been prepared formed of a protective layer and an active layer as described using the materials set forth in the above embodiments. Carriers have also been prepared formed of a protective layer, an active layer, and a mucoadhesive layer using the materials set forth in the above embodiments.

In certain embodiments, the protective layer is formed, followed by formation of the active layer and, in certain embodiments the mucoadhesive layer too, on the protective layer via electrospinning. In other embodiments, the protective layer is formed via electrospinning, followed by formation of the active layer via electrospinning, and coating a mucoadhesive layer on the active layer.

Bioavailability of active agent in the carriers described above in the above embodiments can be evaluated by any sufficient model system or in live subjects.

Figure 2:
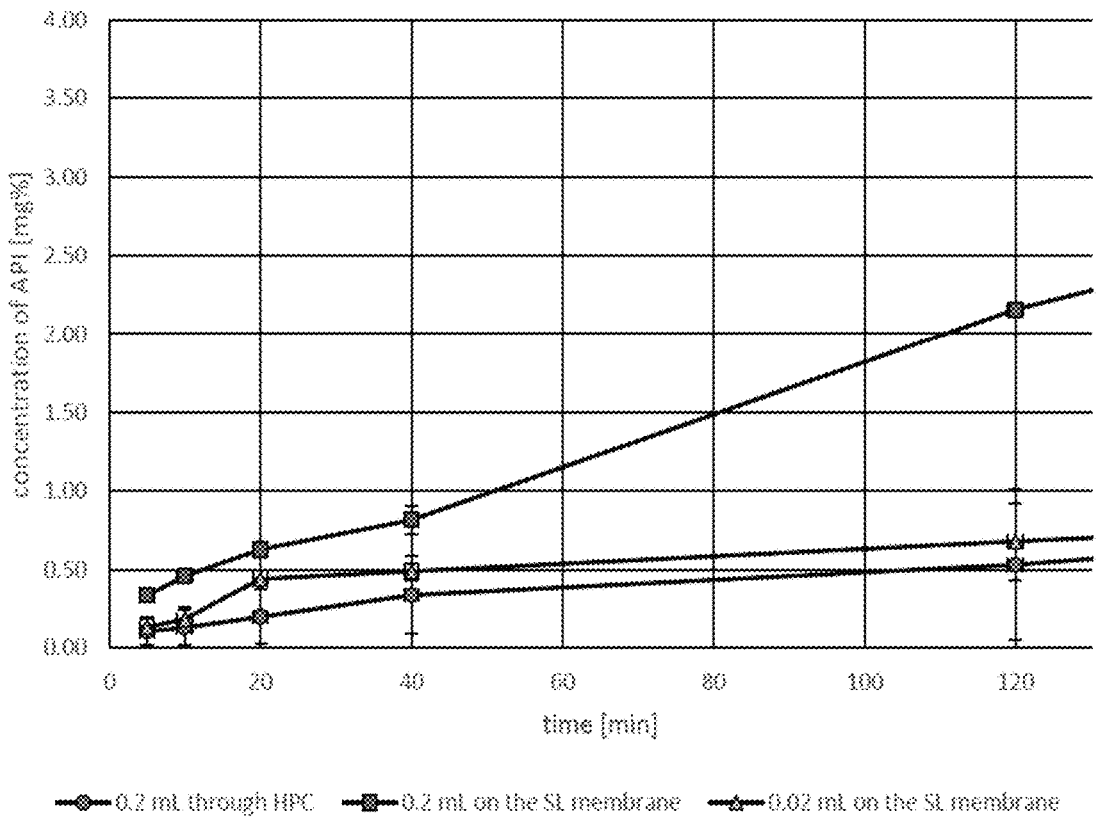
FIG. 2 depicts an in vitro drug absorption concentration versus a time curve for a carrier of the present disclosure. A comparison of moisturizing a covering layer (HPC) and a simple layer placed on the sublingual membrane are depicted. The concentration of Rizatriptan is measured in the acceptor compartment of a Franz diffusion cell (i.e. concentration of Rizatriptan permeation/absorption through a porcine sublingual membrane).

One model system involves using porcine sublingual tissue fixed in Franz diffusion cells with artificial saliva at a pH of 6.8 in a donor compartment and isotonized buffer at a pH of 7.4 (as a blood analogue) in an acceptor compartment. The concentration of the active agent that diffused into the acceptor medium was evaluated over time. FIG. 2 provides exemplary results from such an evaluation. FIG. 2 shows that the amount of permeated rizatriptan is higher when the carrier (having a protective layer comprising HPC polymer) is moisturized by artificial saliva with subsequent application of the carrier to the test medium compared to exposing a previously applied carrier to the saliva. These data correlate with the HPC (containing) protective layer being effective in inhibiting or preventing penetration of saliva to the location of adherence of the carrier in the mouth.

Figure 3:
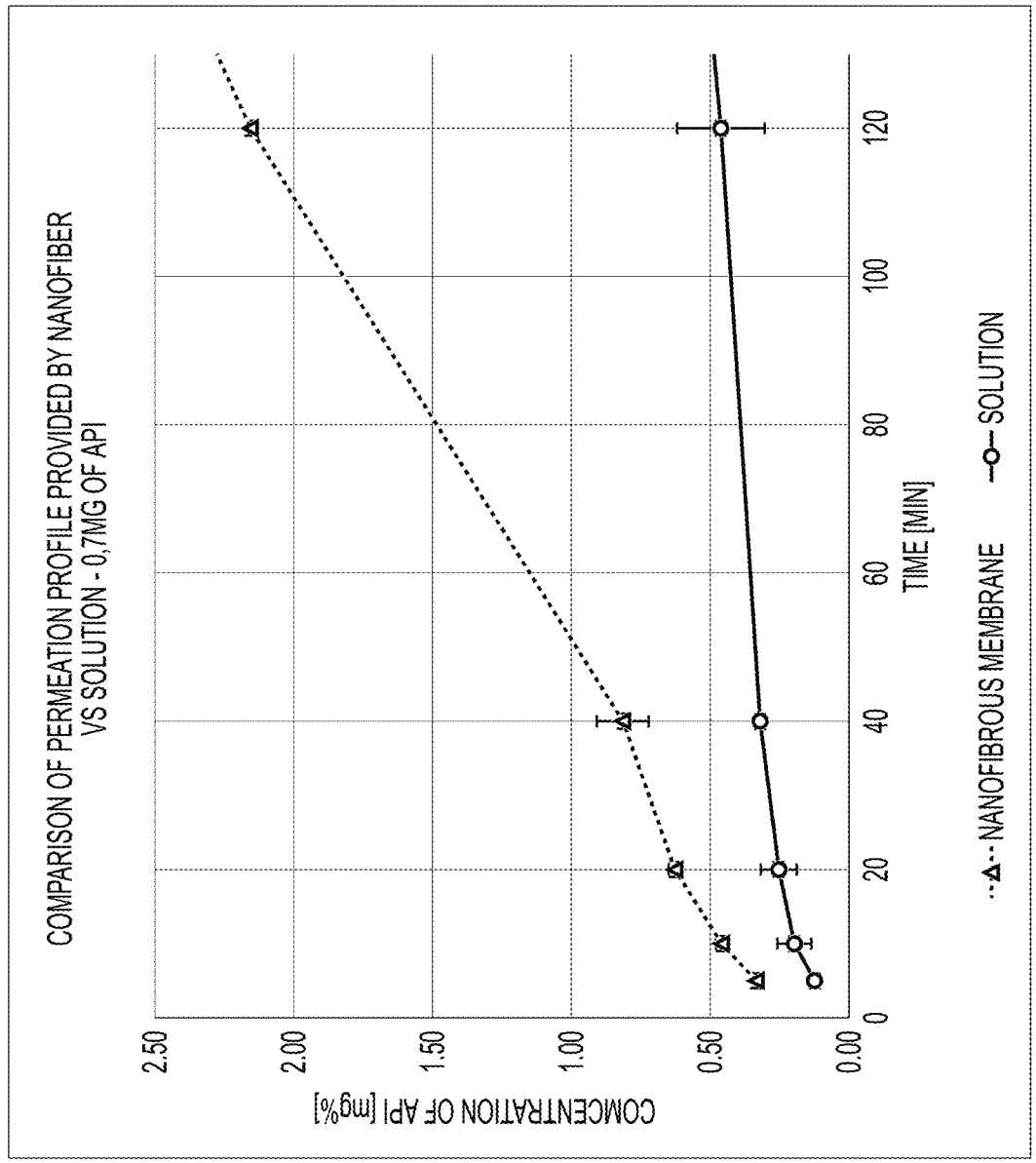
FIG. 3 depicts a drug absorption concentration versus time curve for a carrier of the present disclosure. A comparison of permeation/absorption profiles provided by carrier vs solution (no carrier) of 0.7 mg Rizatriptan is provided.

In another evaluation, a comparison of resulting (physiological) concentrations of active agents "absorbed" in a model system was prepared. In the comparison, rizatriptan solution was applied directly to a medium compared with the introduction of rizatriptan through a carrier (formed as described above) of the present disclosure. Both were applied in the presence of artificial saliva. The same amount of rizatriptan was used for both applications. FIG. 3 depicts a graph of active agent in the medium over time. FIG. 3 shows that the carrier containing the rizatriptan provides an improved permeation of rizatriptan (e.g., through a porcine sublingual membrane) compared with direct application.

In one example, a clinical study was devised for the dosing of rizatriptan to subjects using carriers described herein. One study objective is to evaluate the pharmacokinetic properties of the carrier including the active agent and to compare the bioavailability of a test carrier with a reference product in healthy volunteers under fasting conditions. The reference product is MAXALT® (rizatriptan benzoate, Merck) 5 mg tablets.

The protocol is a two-treatment, two-period cross-over, comparative bioavailability study. A minimum of 2 days is provided in the study as a washout period to clear the active agent from the subjects prior to cross-over administration. Up to about 12 subjects, or more, are included in the trial. Eighteen sampling points are planned: pre-dose; and post-administration at 15 min, 30 min, 45 min, 1 hour, 1.25 hours, 1.5 hours, 1.75 hours, 2 hours, 2.5 hours, 3 hours, 4 hours, 6 hours, 8 hours, 10 hours, 14 hours, 20 hours, and 24 hours.

Each subject that completes the protocol is analyzed and statistically evaluated. Bioavailability is evaluated based on $AUC_{(0-t)}$ and $C_{max}$ of rizatriptan as primary biomarkers. 90% confidence intervals for T/R ratio of LSM for rizatriptan based on ln-transformed data of $AUC_{(0-t)}$ and $C_{max}$ is calculated. An analysis of variance of ln-transformed $AUC_{(0-t)}$ and $C_{max}$ is done using the SAS® GLM procedure. A non-parametric Wilcoxon and median tests of treatment effect for tmax is performed.

Much more important, however, it is that the case specifically shows the real possibility of nanofiber membranes to serve as carriers for drugs which do have promising therapeutic potential, but generally dissolve poorly, especially in aqueous environments.

We mainly consider the obtained and demonstrated results to be a nice example that the usage of nanofiber formulation can allow administration of smaller amount of the drug to achieve the same levels of drug in the central compartment, which brings lower toxicity risks and lowers burden on the human body.

As a further exemplary embodiment, the anticoagulant dabigatran ethexylate mesylate was incorporated in a carrier and compared with micropulver and PRADAXA® (dabigatran, Boehringer Ingelheim) micropellets.

Introduction

Dabigatran ethexylate mesylate (BCS class II) (DG) is a newly approved type of anticoagulant. DG is used to prevent strokes with atrial fibrillation due to other causes than heart valve disease, and at least one additional risk factor for stroke (congestive heart failure, hypertension, age, diabetes, and prior stroke), and to prevent the formation of blood clots in the veins in adults who have had, for example, a hip or knee replacement operation. Its bioavailability after oral administration is low, only about 4% to 7%. Therefore, relatively high doses of the drug are generally needed to achieve sufficient plasma concentration. Under these circumstances the optimal daily dose of DG is in the range of 100 to 300 mg.

Purpose

The aim of the example was to obtain data on dissolution of 10 mg of micropulverized DG substance, and to compare this with DG dissolution/release from PRADAXA® micropellets, and with electrospun polyvinylpyrrolidon nanofiber mats loaded with the same amount of DG.

Methods

In vitro dissolution was performed, measuring the tested samples with the content 10.0 mg of API, in small volume dissolution vessels, 50 ml of phosphate buffer pH 6.0 as dissolution medium at 37±0.5° C. and HPLC determination of DG with UV detection at 320 nm. All the samples were tested repeatedly (n=4 to 5).

Results and Discussion

Figure 4:
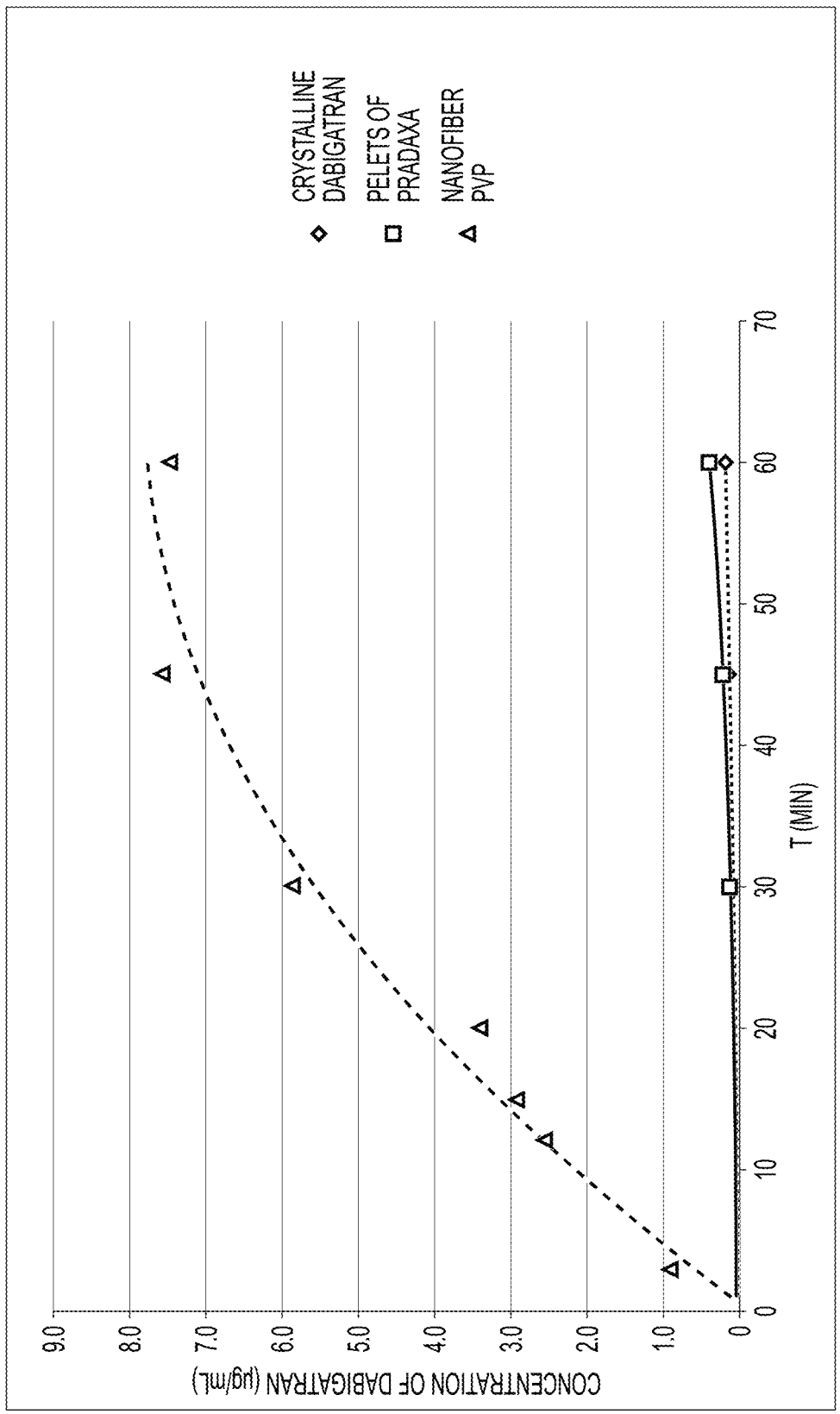
FIG. 4 depicts release profiles of 10 mg dabigatran from micropulverized crystalline substance, micropelets obtained from PRADAXA® (Boehringer Ingelheim Pharma GmbH & Co., KG GMBH & CO. KG) capsules and polyvinylalcohol nanofibre mat in pH 6.0.

The results presented in FIG. 4 show the measured dissolution DG data. The original preparation (PRADAXA®) evaluated for drug release consists of fumaric acid and guar gum core micropelets surrounded with an intermediate isolation layer composed mainly of HPMC (hypromellose) with dimethicon, and an outer active layer of API sprayed onto "pre-pellets" surface using API suspension in HPC (hydroxypropylcelullose). The concentration of the API suspension is understood to be approximately 15%. The manufacturing method of the original micropellet preparation uses a complicated process compared with the commonly used simple spray-drying of solid dispersion. However, in principle, this process has similar features regarding to the amorphization of DG and also to the dispersion type of API/polymer coating of the final micropellets. Fumaric acid enhances the dissolution of the pH-dependent DG due to the decrease of pH in the aqueous medium surrounding the micropellets after oral administration.

The solubility of DG substance is very good at acidic stomach pH. However, the drug absorption problems occur in the small intestine where DG is released from PRADAXA capsules at pH about 6 to 8. The DG precipitation is then followed by dramatically lowered intestinal absorption, thus decreasing the systemic bioavailability and having undesirable side-effects.

FIG. 4 presents release profiles of 10 mg dabigatran from micropulverized crystalline substance, micropellets obtained from PRADAXA® capsules and polyvinylalcohol nanofibre mat in pH 6.0.

The nanofiber membrane generally provides much higher drug dissolution in terms of nanosizing and amorphization. The dissolution rate of DG measured at slightly acidic pH 6.0 is surprisingly fast from the nanofibre samples, the concentration of the dissolved drug is higher by order comparing either to microcrystalline or micropellet form. We consider the usage of DG loaded nanofibre carrier advantageous, depending on mechanism of DG absorption in small intestine.

As another exemplary embodiment, the sublingual transmucosal permeation of liraglutide from an exemplary carrier was evaluated.

Introduction

Liraglutide is a long-acting analog of glucagon-like peptide 1 (GLP-1) and it is used in the treatment of type-2 diabetes mellitus, and obesity. GLP-1 alone is released from gut endocrine L cells and it regulates insulin secretion in a glucose-dependent manner, gut motility and appetite. It has also been demonstrated in animal models to promote neuroprotection against Parkinson and Alzheimer's disease thanks to central effects. The fundamental problem of GLP-1 is its very short biological half-life (in a few minutes), so it cannot be used for treatment. Liraglutide, compared to GLP-1, has two structural modifications, based on addition of palmitoyl moiety at C 16 and exchanging lysine in position 34 with arginine. Those modifications bring a chance for noncovalent binding to albumin, which delays both proteolytic inactivation and renal clearance.

Purpose

To date, there is little known on non-invasive administration of liraglutide. The aim of this work included: (1) to identify composition and processing parameters to formulate liraglutide enclosed in a nanofibre carrier of pharmaceutically approved excipients using large scale electrospinning technology; and (2) to estimate in vitro release liraglutide potential from the nanofibre carrier and the potential of these GLP-1 analog to further permeate through porcine sublingual mucosa.

Methods

Nanofibres in this example comprise a mixture of HPMC (hydroxypropylmethyl cellulose) and PEO (polyethylene oxide) (Sigma Aldrich), and Liraglutide (obtained from PolyPeptide, US). Nanofibres were produced using electrospinning technology and parameters described herein. SEM evaluation was performed using a variety of magnifications.

The liraglutide containing nanofibre carrier samples or the reference solution samples were applied onto fresh porcine sublingual mucosa of thickness ca 0.4 mm fixed in a Franz diffusion cell. An exposed mucosal area for permeation was 1.0 $cm^2$, and the stirred acceptor phase was phosphate buffer pH 7.4 tempered at 37°±0.5° C. Both the tested solutions (Victoza pre-filled pen for subcutaneous injection, 6 mg/mL and the liraglutide solution in buffer pH 6.80, 0.4 mg/mL) were applied onto the sublingual membrane in 400 µL volume. Donor nanofibre samples contained 0.5 mg of liraglutide in the form of a multilayered nanofibre disc and were suffused in donor space with 400 µL of buffer pH 6.80 or 8.15, respectively.

Determination of liraglutide was performed on an Agilent 1200 instrument. The parameters were as follows: Column Poroshell 120 EC-C18 (4.6×150 mm, particle size: 5.0 µm) was thermostated at 35° C. Samples were kept at 10° C., injection 5.00 µL. Mobile Phase A: $Na_2HPO_4$ (pH 7.75): ACN (85:15) was mixed with Mobile Phase B: ACN in gradient and pumped at speed 1.200 mL/min. Detector wavelength: 215 nm. Resulting liraglutide retention time was ca 3.4 min.

Figure 5:
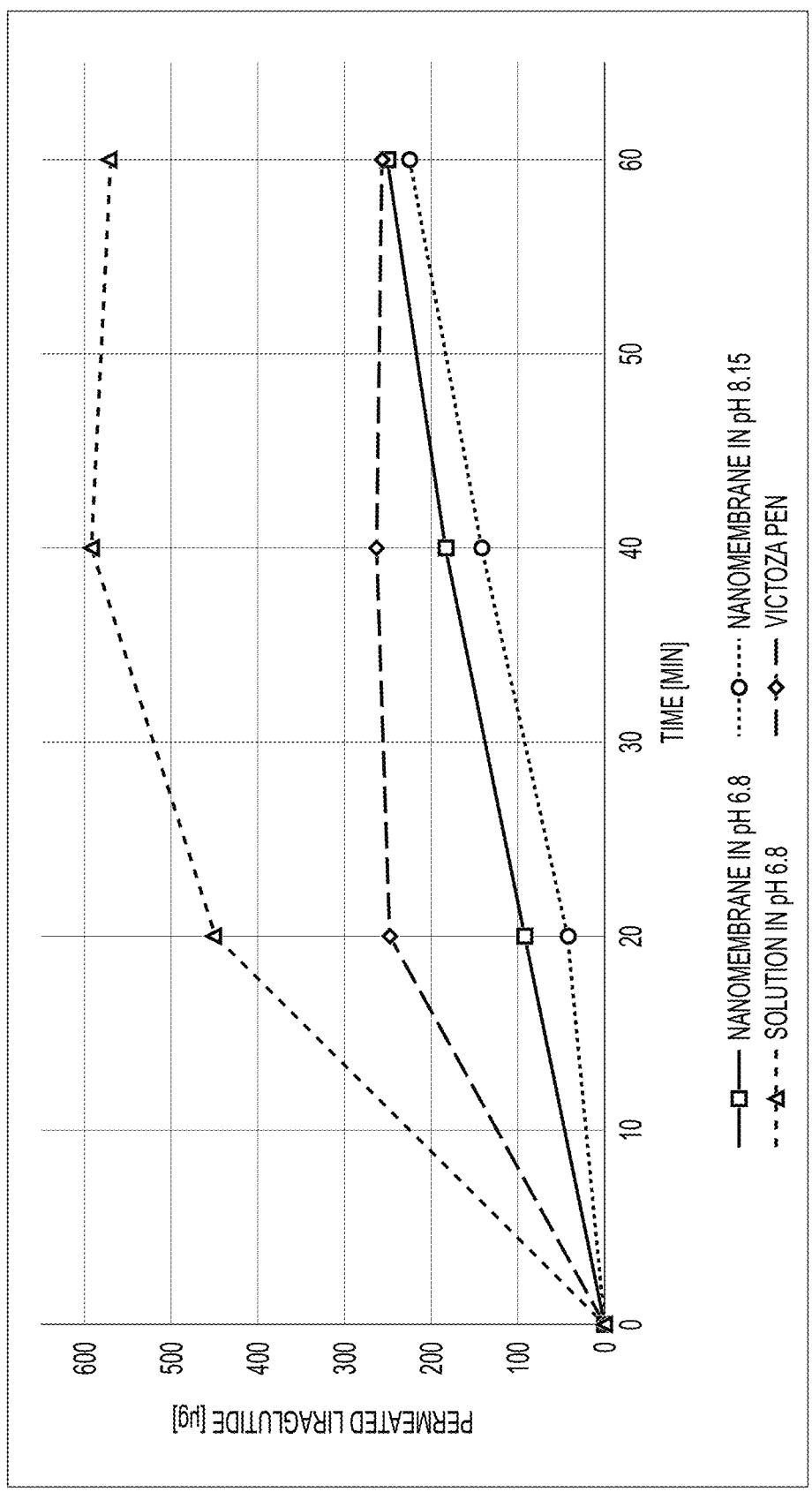
FIG. 5 depicts a comparison of in vitro transmucosal permeation liraglutide profiles from nanofibres and solutions, recalculated to donor amount of 1.2 mg of liraglutide.

The primary data from HPLC analysis of the acceptor samples were further corrected for sampling and replacement of the acceptor phase and values presented in FIG. 5 were calculated. All the samples were tested repeatedly (n=4 to 5).

Results and Discussion

We optimized composition and electrospinning variables to produce a nanofibre membrane bearing high contents of liraglutide and with handling properties suitable for easy sublingual administration in humans.

The amount of liraglutide incorporated into nanofibers was cca 10% of dry weight, however, higher load concentrations above 10% are contemplated and possible using the methods described herein.

Membranes produced by the present electrospinning technology estimated by SEM show homogeneously distributed nanofibres with regular nanofibre diameters and regular porosity.

With the resulting carriers, we found liraglutide able to permeate transmucosally through the sublingual membrane.

This finding can be discussed within the context of possible liraglutide agglomeration into more complex and larger units (e.g. hexamers, heptamers).

The present electrospinning technology enables well reproducible large scale production of nanofibres with the content up to about 10 percent of liraglutide in dry weight. Nanofibre membranes are of very good morphological (SEM) and macroscopic quality.

Liraglutide releases from the tested nanofibre carrier immediately after contacting aqueous liquid on the sublingual membrane and it can permeate further sublingually in in vitro conditions for about 1 hour.

REFERENCES

Jang, H.-J. et al., Proc. Natl. Acad. Sci. USA. 104, (2007), 15069-15074.
Moran-Ramos, S. et al., Adv. Nutr. Int. Rev. J., 3, (2012), 8-20.
Christian Holscher, J. Endocrinology 221, (2014), T31-T41.
McClean, P. L., Holscher, C. Neuropharmacology. 76, (2014), 57-67.
Ahren, B., Exp. Cell Res. 317 (2011).:1239-1245.
Tasyurek, H. M. et al., Diabetes Metab. Res. Rev. 30:354-371.
Madsbad, S. Diabetes Obes. Metab., 16 (2014), 9-21.
Vrbata, P. et al., Int. J. Pharm., 457 (2013) 168-176.

As another exemplary embodiment, the sublingual transmucosal permeation of bovine serum albumin (BSA) from an exemplary carrier was evaluated.

Introduction

Albumin is an attractive macromolecular carrier that has been shown to be biodegradable, nontoxic, metabolized in vivo to produce innocuous degradation products, nonimmunogenic, easy to purify and soluble in water.

Human serum albumin (HSA) and its bovine analog (BSA) are non-glycosylated onechain plasma proteins (relative MW of 66.5 kDa and 69.3 kDa, resp.) exhibiting an average half-life of 19 days. Both of the albumins are very soluble globular proteins that are extremely robust towards pH (stable in the pH range of 4-9), temperature (can be heated at 60° C. for up to 10 h), and organic solvents. They also have an isoelectric point (pI) of ca 4.7 in water (at 25° C.

The physiological functions and properties of HSA and BSA are multifold. They have extraordinary ligand binding capacity, providing a depot for a wide variety of compounds that may be available in quantities well beyond their solubility in plasma. Therefore, albumins have been extensively studied as a carrier of a great number of drug APIs (e.g., benzodiazepines, penicillins, among many others). The accumulation of albumin in solid tumors led to developing albumin-based drug delivery systems for tumor targeting. For instance, methotrexate-albumin conjugate, an albumin-binding prodrug of doxorubicin, or albumin paclitaxel nanoparticles have been clinically used, though always parenterally.

Purpose

The aim of this study, using BSA as a model carrier protein, was to obtain data regarding: (1) the ability of electrospinning technology to create albumin containing nanofibre mat of quality usable for pharmaceutical purposes; (2) the ability of the obtained carrier nanofibre product to release BSA in the form potentially permeable through sublingual (SL) mucosa in vitro; and assess (3) apparent upper permeation limit of BSA as carrier for sublingual drug delivery.

Methods

Nanofibres in this example consist of 5 parts (by weight) of BSA, 5 parts FITC-BSA (fluorescent isothiocyanate-BSA) in polymer mixture of PEO (polyethylene oxide) and PVA (polyvinyl alcohol). All substances were purchased from Sigma Aldrich. Nanofibres were produced using electrospinning technology and parameters described herein.

In Vitro Permeation Experiments

Many of technical details were described previously, however in sum, small cut pieces porcine sublingual mucosal membrane of thickness ca 0.4 mm from the lower side of fresh porcine tongues were mounted into modified Franz diffusion cells. An exposed area for permeation was provided at 1.0 cm$^2$. Donor samples of either the multiple layered nanofibre membrane or the reference FITC-BSA solution contained ca 4.8 mg of total albumin, and the stirred acceptor phase (of 37°±0.5° C.) was phosphate buffer pH 7.4. All the samples were tested repeatedly (n=4 to 5).

HPLC Determination

Determination of FITC-BSA was performed on an Agilent 1200 instrument with FLD detector (Agilent Technologies, USA). The FLD detector wavelength was set at 495 nm for excitation and 523 nm for emission. The primary data from HPLC analysis of the acceptor samples were further corrected for sampling and replacement of the acceptor phase. Permeation profiles [µg of permeated total albumin vs. time] are presented in FIG. 6.

Results and Discussion

We found suitable composition and manufacturing conditions for the production of a nanofiber membrane having reasonably high content of BSA (up to ca 30 percent of dry weight). This indicates that albumins can be incorporated into nanofibres using the present methods using large scale production electrospinning technology.

The resulting FITC-BSA-containing nanofibre mats appear optically without any clumps and of a suitable diameter homogeneity, and thus provide unique properties of this physical-chemical material state. The nanofibre loading capacity for albumin can be further increased and additional nanofibre carriers are produced in further contemplated exemplary embodiments.

Figure 6:
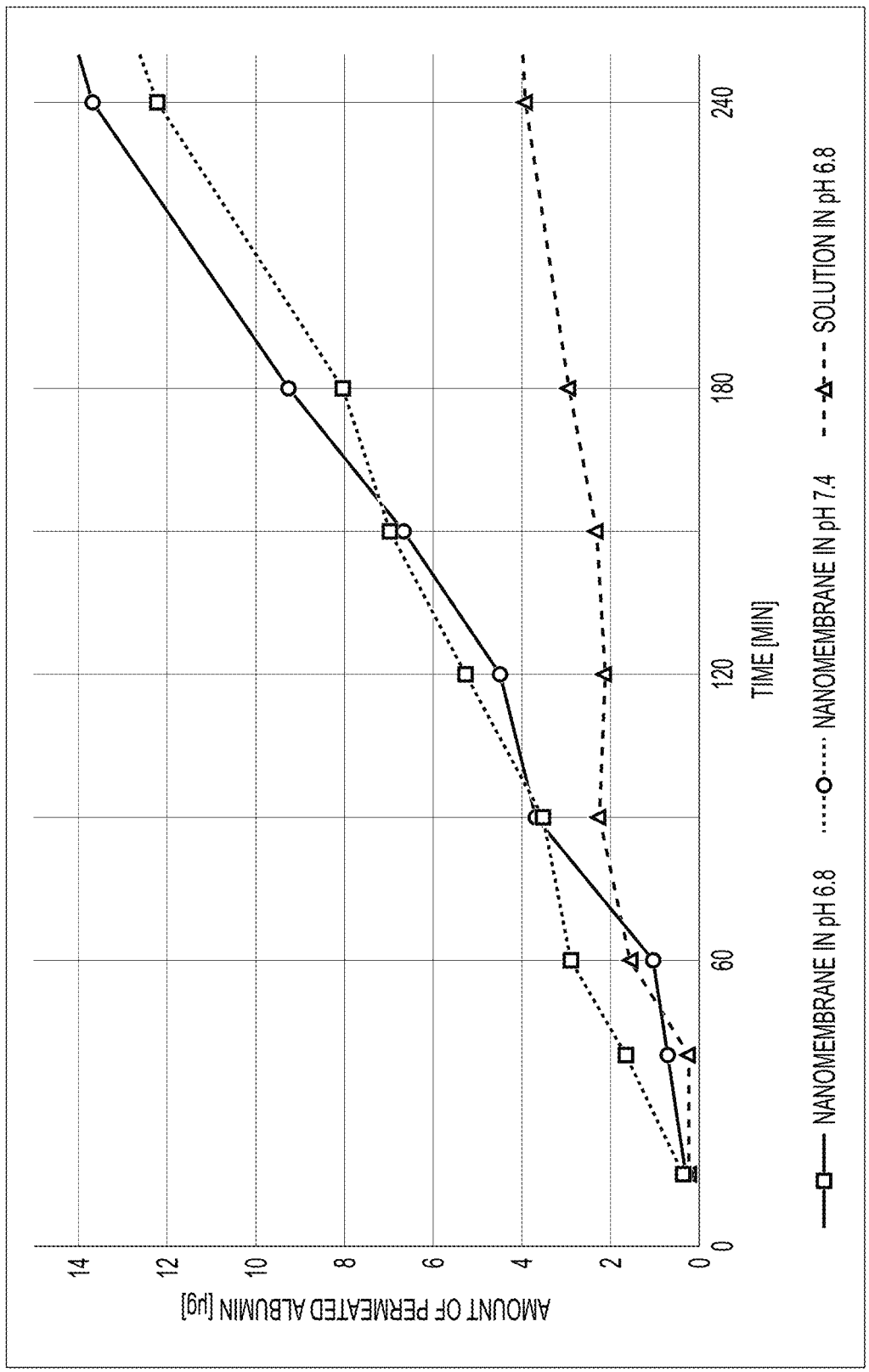
FIG. 6 depicts permeation of bovine serum albumin through a porcine sublingual membrane in vitro.

The transmucosal in vitro permeation of FITC-BSA through sublingual porcine membrane was well measurable and is shown on FIG. 6. The obtained permeation profiles imply successful release of albumin from the nanofibres and subsequent creation of such space arrangement of albumin that allows its diffusion across the mucus and further permeation through SL membrane. Moreover, BSA permeation was detected, for example, 20 minutes after loading the donor samples onto mucosa.

While not being bound by any particular theory, serum albumin circulates within blood vessels without a tendency to leak through endothelial barrier outside (into extracellular spaces), so albumin directly entering the bloodstream after sublingual mucosae permeation is of lower probability. Nevertheless, large albumin-like molecules can be expected to be further absorbed via lymphatic vessels with final passing of macromolecular particles at lymphatic connection to vena subclavia (either left or right sided).

The properties of albumin as drug carrier has been well discussed, so the inventors expect that smaller elipsoidal albumin-like body would, in frequent embodiments, carry a hydrophobic API enclosed and non-covalently (reversibly) kept in a core while surface of such particle is covered with hydrophilic protein moieties. Thus, providing API not only to pass the SL barrier but also reach systemic circulation.

Electrospinning using large scale electrospinning technology and parameters described herein supports the production of albumin containing nanofibres of a very good morphological (SEM) quality. Albumin was found to release easily from the resulting carriers and permeate sublingually at a high level.

REFERENCES

Langer, K. et al., Int. J. Pharm., 347 (2008) 109-117.
Kratz, F., J. Control. Release 132 (2008) 171-183.
Vrbata, P. et al., Int. J. Pharm., 457 (2013) 168-176.
Elzoghby Ahmed O. et al., J. Control. Release 157(2012) 168-82.

Figure 7:
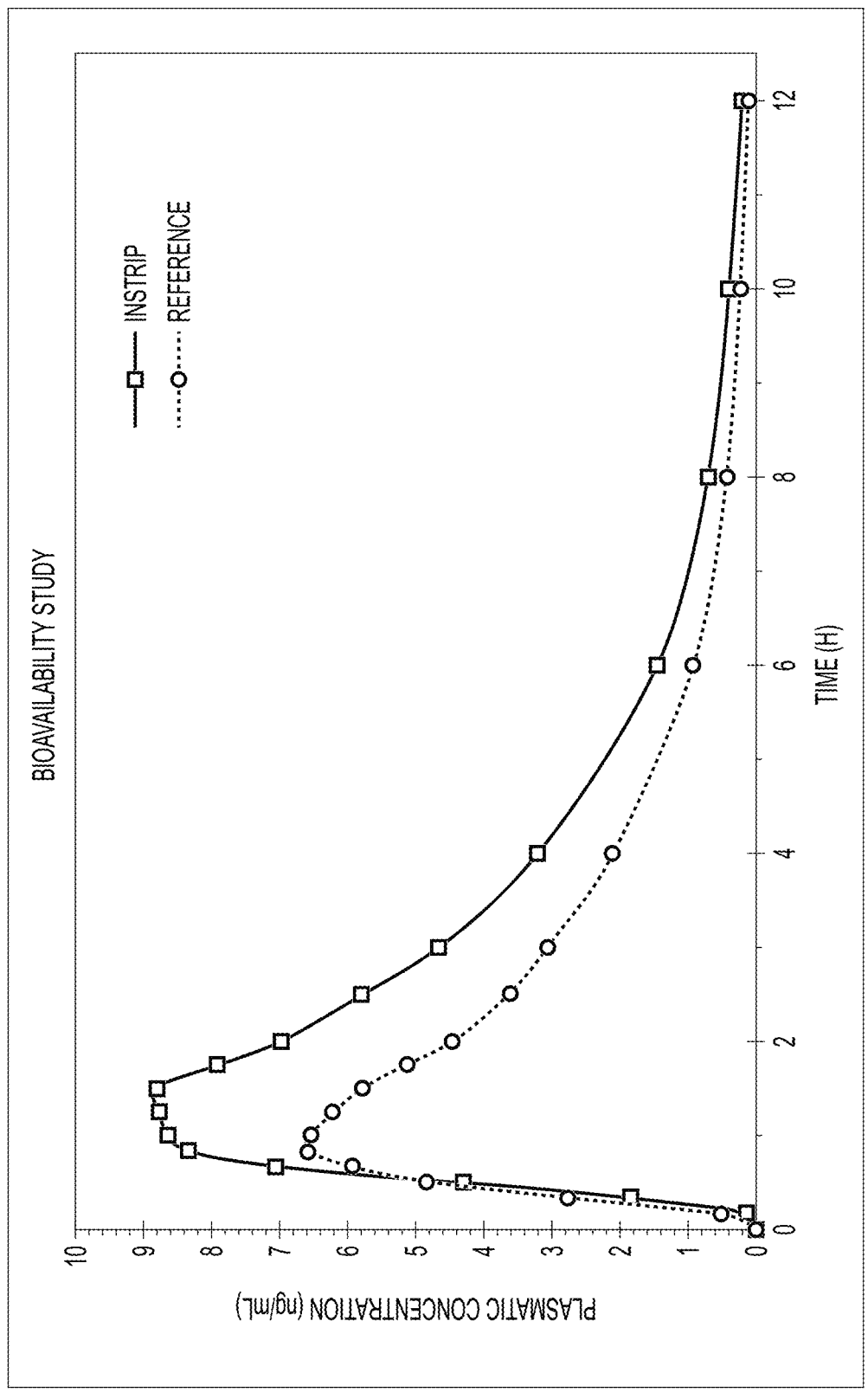
FIG. 7 provides an active agent blood plasma concentration curve.

Bioavailability of active agent delivery using carriers of the present was investigated. In a clinical trial, 5 mg of an active agent (rizatriptan) included in a carrier as described herein was compared to a reference orodispersible lyophilized tablet product currently on the market. The trial involved 12 volunteers who received the carrier, after several days of competitive product. Plasma was collected from the cubital vein, which was then analyzed and was examined significant pharmacokinetic parameters $C_{max}$, AUC. FIG. 7 provides an active agent blood plasma concentration curve from this investigation. The carriers achieved drug plasma concentration ($C_{max}$) and measured area under the curve (AUC) that is significantly higher than the reference product, for example as indicated in the following Table.

| Parameter | Test | Ref. | RATIO T/R (%) |
|---|---|---|---|
| $AUC_{(0-t)}$ (ng · h/mL) | 28.255 | 19.467 | 145.15 |
| $C_{max}$ (ng/mL) | 10.193 | 7.001 | 145.59 |

The above examples are included for illustrative purposes only and are not intended to limit the scope of the disclosure. Many variations to those described above are possible. Since modifications and variations to the examples described above will be apparent to those of skill in this art, it is intended that this disclosure be limited only by the scope of the appended claims.

Citation of the above publications or documents is not intended as an admission that any of the foregoing is pertinent prior art, nor does it constitute any admission as to the contents or date of these publications or documents.

We claim:

1. A method of orally administering an active agent to a subject in need thereof, comprising:
    administering to a mouth of the subject a nanofiber carrier, the nanofiber carrier comprises:
    a nanofiber active layer containing a water soluble polymer and/or biodegradable polymer and an active agent;
    a nanofiber protective layer; and
    a mucoadhesive layer,
    wherein the active agent is a biopolymer having a molecular weight of between 627 Da to 70 kDa, a bovine serum albumin (BSA), glucagon-like peptide 1, a glucagon-like peptide 1 analog, or dabigatran ethexylate mesylate,
    wherein the glucagon-like peptide 1 analog is one or more of liraglutide, exenatide, lixisenatide, albiglutide, dulaglutide, taspoglutide, and/or semaglutide,
    wherein the mucoadhesive layer is comprised in or on the nanofiber active layer, and
    wherein the nanofiber active layer is prepared by wire electrospinning a polymer solution having sodium dihydrogen phosphate.

2. The method of claim 1, wherein the carrier further comprises a nanofiber protective layer comprised of a polymer selected from the group comprising: (a) a water insoluble polymer or polymer treated to be water insoluble; or (b) two or more of hydroxypropylcellulose, carboxymethylcellulose, polyvinyl alcohol-polyethylene glycol, polyvinyl alcohol, and polyethylene oxide;
    wherein the nanofiber active layer becomes solubilized within the mouth cavity of the subject, and the protective layer is insoluble in the mouth of a subject and impermeable to saliva and the active agent,
    wherein the active agent is released from the nanofiber active layer after it becomes solubilized.

3. The method of claim 2, wherein the active agent further comprises a sodium pump inhibitor, an anticonvulsant, an antidepressant, a beta-blocker, a calcium channel blocker, a nonsteroidal anti-inflammatory drug (NSAID), a serotonin receptor antagonist, a serotonin reuptake inhibitor, a serotonin noradrenaline reuptake inhibitor, an analgesic, an antiemetic, an ergot derivative, a neuropeptide antagonist, a migraine medication and/or riboflavin.

4. The method of claim 1, wherein the nanofiber comprises between 5% by weight to 20% by weight of the bovine serum albumin and comprises between 80% by weight to 95% by weight of the water soluble and/or biodegradable polymer.

5. The method of claim 4, wherein the glucagon-like peptide 1 analog, if present, comprises liraglutide; and wherein the BSA, if present, is a drug carrier for one or more different additional active agent.

6. The method of claim 5, wherein the additional active agent comprises a benzodiazepine, a penicillin, a methotrexate, a paclitaxel, a doxorubicin.

* * * * *